US006326188B1

(12) United States Patent
Wolfinbarger, Jr. et al.

(10) Patent No.: US 6,326,188 B1
(45) Date of Patent: Dec. 4, 2001

(54) CONTINUOUS-MULTI-STEP DILUTION PROCESS AND APPARATUS, FOR THE REMOVAL OF CRYOPROTECTANTS FROM CRYOPRESERVED TISSUES

(75) Inventors: Lloyd Wolfinbarger, Jr., Norfolk; Perry Lange, Virginia Beach, both of VA (US)

(73) Assignee: LifeNet, VA (US)

( * ) Notice: Subject to any disclaimer, the term of this patent is extended or adjusted under 35 U.S.C. 154(b) by 0 days.

(21) Appl. No.: 09/169,939

(22) Filed: Oct. 13, 1998

Related U.S. Application Data

(62) Division of application No. 08/822,684, filed on Mar. 24, 1997, now Pat. No. 5,879,876.
(51) Int. Cl.$^7$ ........................................................ A01N 1/02
(52) U.S. Cl. ........................................ 435/284.1; 435/307.1
(58) Field of Search ................................... 435/1.2, 40.5, 435/40.52, 284.1, 288.1, 286.5, 297.2, 304.1, 307.1; 366/165.1; 396/626–629

(56) References Cited

U.S. PATENT DOCUMENTS

| | | | |
|---|---|---|---|
| 671,075 | * | 4/1901 | White . |
| 671,466 | * | 4/1901 | Brockett . |
| 2,205,053 | * | 6/1940 | Thackeray . |
| 2,469,825 | * | 5/1949 | Hornstein . |
| 3,207,487 | * | 9/1965 | Ranson . |
| 3,905,477 | * | 9/1975 | Graham . |
| 5,460,625 | * | 10/1995 | Johnson . |
| 5,470,151 | * | 11/1995 | Walthall et al. . |
| 5,515,877 | * | 5/1996 | Dunn, Jr. . |

* cited by examiner

Primary Examiner—William H. Beisner
(74) Attorney, Agent, or Firm—Susanne M. Hopkins

(57) ABSTRACT

The present invention is directed to a continuous, multi-step dilution process for producing tissue suitable for transplantation into a human from cryopreserved tissue. Cryopreserved tissue is subjected to a continuous flow of wash-out solution following a thawing or simultaneously thawing using the present continuous perfusion chamber. The present continuous perfusion chamber may be rigid or deformable and has an inlet port and an outlet port.

5 Claims, 11 Drawing Sheets

CONTINUOUS-MULTI-STEP DILUTION PROCESS AND APPARATUS, FOR THE REMOVAL OF CRYOPROTECTANTS FROM CRYOPRESERVED TISSUES

This application is a divisional application of parent application U.S. Ser. No. 08/822,684, filed on Mar. 24, 1997, now issued as U.S. Pat. No. 5,879,876, on Mar. 9, 1999.

FIELD OF THE INVENTION

This invention relates to a method for preparing cryopreserved tissue for transplant into a human. The process is directed to the thawing and removal of cryoprotective agents from cryopreserved tissue. Cryoprotective agents, for example, dimethyl sulfoxide and glycerol, are removed from cryopreserved tissues including for example, cardiovascular tissue including heart valves, arteries and veins, and musculoskeletal tissue, following or simultaneously with thawing from the cryopreserved state by use of a continuous flow-through of wash-out solution using the present continuous perfusion chamber. The present continuous perfusion chamber may be either rigid or deformable, and includes an inlet port and an outlet port.

BACKGROUND OF THE INVENTION

Cryopreserved tissues are defined as tissues which have been frozen in the presence of one or more cryoprotective agents. Cryoprotective agents are defined as compounds which are used to reduce damage to cryopreserved tissues/cells during the freezing, storage, and/or thawing processes associated with cryopreservation.

A variety of tissues are preserved by cryopreservation in the presence of cryoprotective agents. Methods and protocols for the cryopreservation of human heart valves have been extensively described in the scientific literature since the early 1970's, however the method described in U.S. Pat. No. 4,890,457 is representative of these early methods. Of concern to the present invention is the removal of cryoprotective agents from such tissues following or simultaneous with thawing just prior to transplantation into a patient. Most cryoprotective agents used to protect the cryopreserved tissue during cryopreservation are harmful to tissues surrounding the implant due to time and temperature dependent chemical and physical damage and it is generally deemed important to remove these agents from the thawed tissue prior to transplantation. Cryoprotectant removal techniques that have been described include, procedures where the concentration of cryoprotectant is reduced via a timed series of additions of lower osmolality solutions, and procedures where removal is accomplished by adding the tissues to a given volume of lower osmolality solution such as described in U.S. Pat. No. 5,160,313. The approach using a series of additions of solutions to remove cryoprotectant from tissues is time consuming and requires particular attention to details such as elution time, temperature, and composition of the diluting solution. The approach using a given volume requires less attention to details such as elution time, temperature, and composition of diluting solution, however the osmotic shock to the cellular population is rapid and can lead to dramatic cell swelling and subsequent cell damage and/or death (osmotic shock). This osmotic shock may be mitigated by including impermeant solutes in the diluting solution, however, such diluting solutions typically result in a tissue containing an osmotic pressure of between 400 to 800 mOsm which is dramatically greater than the approximate 290 mOsm associated with normal tissue. The present inventive method solves the problem associated with prior art methods by providing a user-friendly, continuous-multi-step dilutional process for removing cryoprotective agents from cryopreserved tissue while maintaining the resultant osmotic pressure within an acceptable normal range. Using a wash-out solution of 280–290 mOsm/kg water results in greater osmotic shock but yields "final" tissue which is iso-osmolar. Using wash-out solution of 500–600 mOsm/kg water lessens the initial osmotic shock but results in "final" tissue which is hyperosmolar.

SUMMARY OF THE INVENTION

A continuous-multi-step dilutional process for removing cryoprotective agents from cryopreserved tissues is disclosed where tissue which has been cryopreserved in the presence of one or more cryoprotective agents is thawed and washed in a continuous perfusion chamber by flowing a wash-out solution of approximate iso-osmotic 280–290 mOsm/kg water or hyper-osmotic 550–800 mOsm/kg water through and around the tissue such that the cryoprotectant is reduced to a nontoxic level of 3.0% (volume to volume) or less in the tissue prior to transplantation. The invention includes both a continuous perfusion chamber and a method whereby the rate of flow of wash-out solution is automatically controlled by the continuous perfusion chamber and a standardized operating pressure for the invention.

The present invention is directed to a continual but slow removal of cryoprotectant from cryopreserved tissues using a continuous-multi-step dilution process where the diluting or wash-out solution is continually perfused through and around the tissue being processed such that the osmolality of the perfusing solution is gradually reduced during the washing and/or thawing process and the cryoprotectant concentration in the tissue is reduced to a level known to be nontoxic to cells present in that tissue.

The present invention is also directed to a process for simultaneously thawing the cryopreserved tissue and removing the cryoprotectants using the present and continuous-multi-step dilution process.

The present invention is directed to a continuous-multi-step dilution process which requires a minimum number of physical steps and can be used on cryopreserved tissue or thawed cryopreserved tissue.

The present invention is further directed to a continuous-multi-step dilution process which requires a minimum number of steps, minimum attention to detail by the attending personnel, and is highly reproducible.

The present invention is also directed to a continuous-multi-step dilution process which requires no monitoring of final cryoprotectant concentrations in the tissue.

The present invention is directed to a continuous perfusion chamber which when used in the continuous-multi-step dilution process, results in controlled perfusion of the tissue being processed and maintains sterility of the tissue up to the time of actual transplantation.

The present invention is directed to a single-use or multi-use rigid continuous perfusion chamber having an inlet port and outlet port.

The present invention is directed to a rigid perfusion chamber having an inlet port and outlet port where the angle of the inlet port causes a circular motion in the chamber thereby causing a stirring effect during the wash-out process.

The present invention is also directed to a deformable continuous perfusion chamber having an inlet port and an outlet port. Preferably, the inlet and outlet port are configured so as to cause a circular motion in the chamber during the continuous-multi-step dilution process, i.e. a "stirring effect." Such configuring is readily accomplished by one of ordinary skill in the art to which the present invention pertaining without undue experimentation.

The present invention is further directed to a continuous-multi-step dilution process using the present continuous perfusion chamber where the chamber further includes a sterile basin in which the present continuous perfusion chamber is placed, where the basin is of a size sufficient such that at the end of the present process the waste wash-out solution is at a level below the outlet port of the present continuous perfusion chamber.

The present invention is directed to a continuous perfusion chamber having an inlet port and outlet port where in-flow tubing is attached to the inlet port and out-flow tubing is attached to the outlet port.

The present invention is directed to a continuous perfusion chamber having an inlet port and an outlet port where sterile in-flow tubing is attached to the inlet port and no tubing is attached to the outlet port.

The present invention is also directed to a deformable continuous perfusion chamber having an inlet port and an outlet port where the deformable continuous perfusion chamber is placed in a sterile basin using sterile means such that the deformable perfusion chamber is at a level in the basin such that at the end of the continuous-multi-step dilutional process, waste wash-out solution is below the level of the outlet port of the deformable continuous perfusion chamber.

The present invention is also directed to a deformable continuous perfusion chamber having an inlet port and outlet port where in-flow tubing is attached to the inlet port and out-flow tubing is attached to the outlet port where the deformable chamber may or may not be placed in a sterile basin using sterile means to suspend the deformable chamber.

The present invention is directed to a deformable continuous perfusion chamber having an inlet port and an outlet port where in-flow tubing is attached to the inlet port and no tubing is attached to the outlet port where the deformable chamber is suspended using sterile means in a sterile major basin such that at the end of the present continuous-multi-step process, waste wash-out fluid is at a level below the outlet port.

The present invention is also directed to means for suspending a deformable continuous perfusion chamber in a sterile basin where such means may include a sterile tripod, a sterile rack, or other suitable device capable of suspending a deformable continuous perfusion chamber where said means are composed of any material capable of being sterilized by any known method in the art including for example, autoclaving, gas sterilization, and/or UV light sterilization. Preferable material include steel, stainless steel, plastics, composites, ceramics, glasses and ceramic composites. Such means may be separate from the present basin or may be integrally formed with the present basin. Such means may also include a perforated plate placed over the basin, a rack placed over the basin, a screen placed over the basin, a strip or bar placed over the diameter of the basin from which the deformable continuous chamber may be suspended or laid flat, a shallow or perforated, woven or screen type basin of identical diameter maybe placed over the main basin and the deformable chamber may be placed in the shallow basin. Any of the recited perforated means may include any combination of perforations, woven strips, or porous materials, with the requirement that the waste wash-out fluid exiting the deformable chamber, exits at a height so as to preclude any pooling of wash-out solution in the perforated means.

These and other objectives will be apparent to those of ordinary skill in the art from the teachings herein.

BRIEF DESCRIPTION OF THE FIGURES

The present invention is further explained in the description that follows with reference to the figures and drawings, by way of non-limiting examples, various embodiments of the invention, with like reference legends representing similarly collected data throughout the several figures and drawings.

FIG. 1 illustrates a schematic diagram of the present preferred embodiment. The present rigid continuous perfusion 1 chamber including in-flow tubing 2 running from the wash-out solution reservoir 3 to the inlet port 4 of the continuous perfusion chamber 1 where the continuous perfusion chamber 1 is placed in a sterile major basin 5 and the waste wash-out solution runs directly into the major basin through outlet port 6 on the continuous perfusion chamber 1. The continuous perfusion chamber 1 in this embodiment does not include out-flow tubing.

FIG. 2 illustrates a cross-section view of the present rigid continuous perfusion chamber where the perfusion chamber includes a lid 6a which may be placed on the body portion 7 during use, where the lid 6a may simply sit on the body portion 7, where the lid 6a and body portion 7 may be configured such that the lid 6a screws onto body portion 7, or the lid 6a and/or body portion 7 may also include a seal or O-ring to enable the lid 6a to be frictionally fit to the body portion 7. The body portion 7 includes an inlet port 4 and an outlet port 6a where a preferred height 8 of the body portion is about 5.75 inches, a preferred height 9 from the bottom of the body portion to the center of the inlet port is about 0.7 inch, and a preferred height 10 from the bottom of the body portion to the center of the outlet port is about 1.25 inches.

FIG. 3 illustrates a top view of the present rigid continuous perfusion chamber. Where the inlet port 4 and the outlet port 6 are at angles relative to the chamber, appropriate to cause a "stirring effect" during the present process. The inlet port 4 is preferably at angle 11 of about 40° as shown. The outlet port 6 is preferably at an angle 12 of about 90° as shown 13 is as shown about 4.250.

FIG. 4 illustrates a cross-sectional view of the present deformable continuous perfusion chamber 1 which deformable continuous perfusion chamber 1 also functions as the cryopreservation pouch for freezing the cryopreserved tissue and includes inlet port 4 having an inlet septum 14, outlet port 6 having an outlet septum 15, sealed edges 16 (for example, heat sealed or sealed by radio-frequency sealers), inlet connector 17, outlet connector 18, in-flow tubing 2 and out-flow tubing 19. The continuous perfusion chamber/pouch is configured to hold a volume 20 of about 100 mls of liquid.

FIG. 5 illustrates a preferred embodiment of the present deformable continuous perfusion chamber including inlet port 4, outlet port 6, a volume 20 of about 100 mls, cryopreserved heart valve 25, sealed edges 16, and suspension loop 26 for suspending the chamber during the present continuous-multi-step dilution process. The chamber may optionally be suspended over a major basin.

FIG. 6 illustrates the present deformable continuous perfusion chamber including inlet port 4, outlet port 6, suspension loop 26, the direction of flow 27 of wash-out solution during processing including circular pattern of flow 24 within the chamber during use effected by the appropriate configuration of the inlet port and outlet port. Also shown is suspension means 28 and wash-out solution reservoir 3.

FIG. 7 illustrates the present continuous-multi-step dilution process using the present rigid continuous perfusion chamber 1. IV pole 21 has an approximate height 22 of from about 5 to 6 feet and serves to suspend the wash-out solution reservoir 3 which is connected to in-flow tubing 2 running to the inlet port 4 of the continuous perfusion chamber 1. Wash-out solution runs from the reservoir 3, through in-flow tubing 2, and into the continuous perfusion chamber 1 through inlet port 4 creating a circular flow of solution in the chamber and wash-out solution then runs through outlet port 6, through out-flow tubing 19 and into a waste basin 23.

FIG. 8 illustrates the marked portion in FIG. 7 enlarged to show the circular flow 24 of solution in the present rigid continuous perfusion chamber 1, the circular flow is caused by the angle 11 of the inlet port 4 as shown.

FIG. 9 illustrates DMSO concentration in the wash-out solution exiting the continuous perfusion chamber via the outflow port as a function of volume of wash-out solution. A thawed cryopreserved human heart valve as a total volume of 100 mls in cryopreservation solution was added to the chamber prior to wash-out. The wash-out solution consisted of a one (1) liter bag of Plasmalyte.

FIG. 10 illustrates the osmolality (mOsm/Kg water) of wash-out solution exiting from the continuous perfusion chamber via the outflow port as a function of volume of wash-out solution. A thawed cryopreserved human heart valve as a total volume of 100 mls in cryopreservation solution was added to the chamber prior to wash-out. The wash-out solution consisted of a one (1) liter bag of Plasmalyte supplemented with 7.14% mannitol. (See associated Table 1 for actual values.)

FIG. 11 illustrates the DMSO concentration in the wash-out solution exiting the continuous perfusion chamber via the outflow port as a function of volume of wash-out solution. A thawed cryopreserved human heart valve as a total volume of 100 mls in cryopreservation solution was added to the chamber prior to wash-out. The wash-out solution consisted of a one (1) liter bag of Plasmalyte supplemented with 7.14% mannitol. (See associated Table 2 for actual values.)

FIG. 12 illustrates the osmolality (mOsm/Kg water) of the wash-out solution exiting from the continuous perfusion chamber via the outflow port as a function of volume of wash-out solution. A thawed cryopreserved human heart valve as a total volume of 100 mls in cryopreservation solution was added to the chamber prior to wash-out. The wash-out solution consisted of a one (1) liter bag of LR5. (See associated Table 6 for actual values.)

FIG. 13 illustrates the DMSO concentration in the wash-out solution exiting the continuous perfusion chamber via the outflow port as a function of volume of wash-out solution. A thawed cryopreserved human heart valve as a total volume of 100 mls in cyropreservation solution was added to the chamber prior to wash-out. The wash-out solution consisted of a one (1) liter bag of LR5. (See associated Table 7 for actual values.)

FIG. 14 illustrates temperature profiles of cryopreserved human heart valves during transitioning (Slow 1, Slow 2, Slow 3) as compared to the temperature profile of a similar cryopreserved human heart valve rapidly thawed by immersion is a water bath of saline solution at 37 to 42° C. The time interval totaled 7 minutes.

DETAILED DESCRIPTION OF THE PREFERRED EMBODIMENTS

I. Definitions

Figure 1:
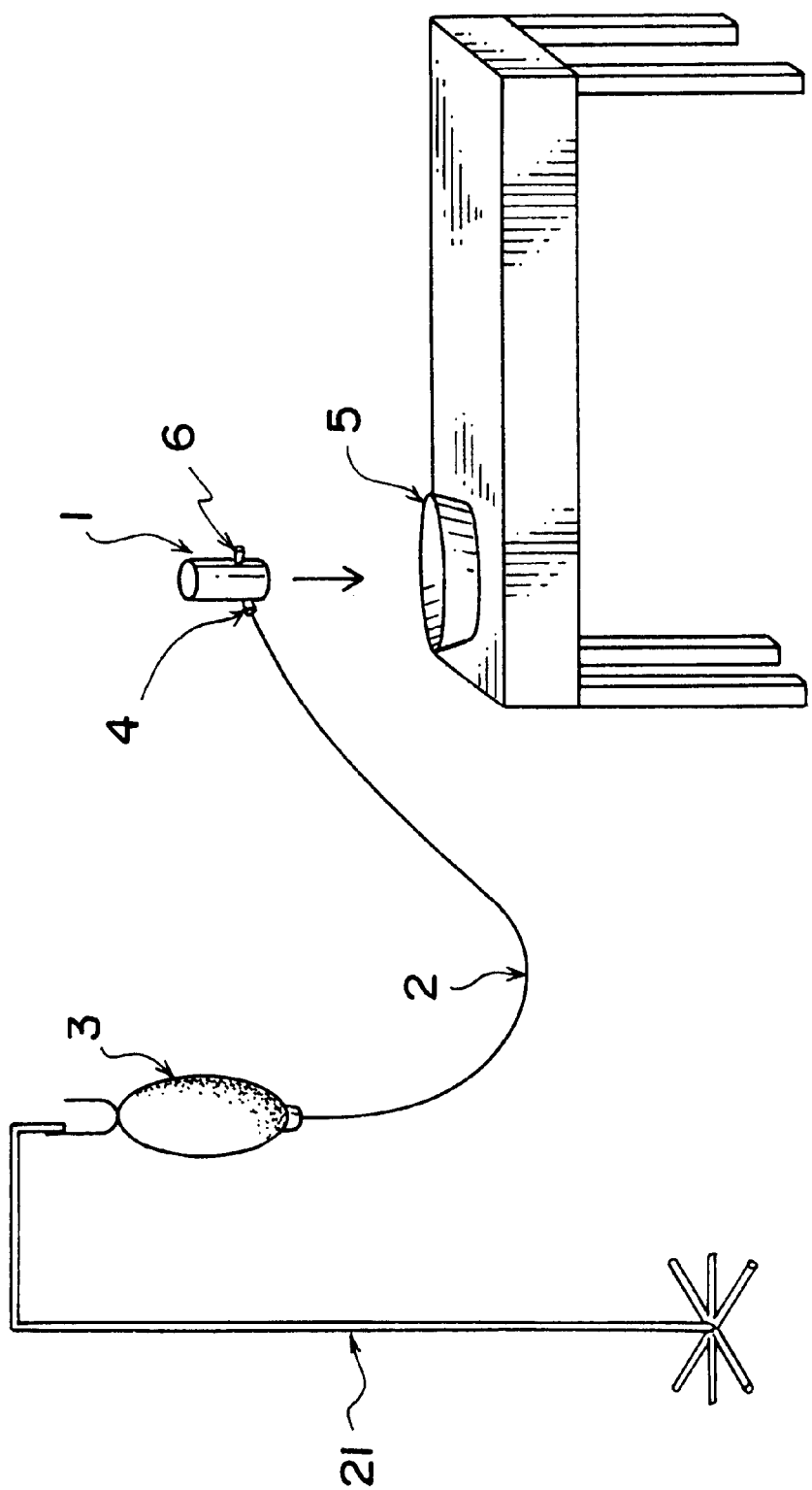
FIG. 1

The below definitions serve to provide a clear and consistent understanding of the specification and claims, including the scope to be given such terms.

Cryopreserved Tissue. As used herein, the term "cryopreserved tissue" refers to biomaterials which contain both noncellular matrix components including for example, collagens, proteoglycans, proteins, elastins and polysaccharides, present as an essentially insoluble material in an aqueous environment, plus a cellular component variously distributed throughout the noncellular matrix, which has been cryopreserved in the presence of a cryoprotective agent. Examples of "cryopreserved tissue" include, but are not limited to, cardiovascular tissues, such as heart valves, veins, aortic grafts, and other musculoskeletal tissues including skin, ligaments, tendons, cartilage and all forms of synthetic tissue.

Continuous Perfusion Chamber. As used herein, the term "continuous perfusion chamber" refers to a device such as illustrated in FIGS. 1–8, or any similar device that provides essentially the same function, but and will accommodate the cryopreserved tissue to be treated using the continuous perfusion process. The present continuous perfusion chamber is designed to permit the continuous change in composition of the wash-out solutions contained in the continuous perfusion chamber by having an inlet port through which solutions can be added to the chamber and an outlet port through which solution can be removed from the chamber. The present continuous perfusion chamber can be rigid and composed of any material capable of being sterilized by any known method including for example, autoclaving, UV light, and gas, such materials including for example, plastics, composites, stainless steel, glasses, ceramics and ceramic composites. The present continuous perfusion chamber can also be deformable for example, a deformable pouch of any shape including square, rectangle, and round and is composed of any deformable material capable of being sterilized by any known methods and capable of maintaining its integrity at ultra low temperatures used in cryopreservation (the material must be able to withstand temperatures from –70 to –150° C. or below preferably temperatures of –150° C. or below and seals must be retained intact.) The inlet and outlet ports of the deformable chamber must also be able to withstand temperatures in the range of –70° C. to –150° C. or below and return the seals intact. The ports may be composed of any suitable material as readily determined and employed by one of ordinary skill in the art without undue experimentation and may include for example, ethylene vinyl acetate. Suitable materials include, for example, vinyl polymers and copolymers including for example, ethylene vinyl acetate; ethylene vinyl acetate copolymer; ethylene, polyethylene and ethylene vinyl alcohol copolymer. The present deformable continuous perfusion chamber can be the pouch used both to cryopreserve the tissue and to prepare the tissue for transplantation. The present deformable chamber is a single-use chamber. The present rigid chamber may be either single-use or multi-use and preferably includes a loose-fitting lid for placement over the chamber. Alternatively, a screw-type lid may be used, or a pressure fitted lid, or any other means known to those skilled in the art to cover the chamber. No lid is also contemplated.

Major Basin. As used herein, the term "major basin" refers to an appropriately sized sterile basin (generally about a five (5) liter basin) in which the present continuous perfusion chamber may be placed during the present continuous-multi-step dilution process. The major basin is sterile and provides an additional element of safety in that if the continuous perfusion chamber is bumped or pushed over any tissue contained therein remains in the sterile major basin and is thus still sterile. Further, the major basin may be used with the continuous perfusion chamber using only in-flow tubing attached to the inlet port of the continuous perfusion chamber at the chamber end and attached to the wash-out solution reservoir at the reservoir end and where no tubing is attached to the outlet port such that sterile waste wash-out solution is emptied directly into the sterile major basin. The major basin may also be used with the present deformable continuous perfusion chamber additionally using means either separate from the major basin or integrally formed with the major basin to suspend the deformable perfusion chamber in the major basin at a level such that waste wash-out solution is at a level below the outlet port of the continuous perfusion chamber. Such means may include a rack, a table, a tripod-like table, a perforated colander type basin insert, an integrally formed major basin with a colander type second shallow basin, a rod or strip bridging the diameter of the major basin from which to suspend or lay flat the present deformable perfusion chamber. Such means may be composed of any material capable of being sterilized if multi use is contemplated including for example, steel, stainless steel, plastics, composites, ceramics, and ceramic composites capable of being sterilized by any known method. If only single use is contemplated, any sterile structurally sufficient material is contemplated. Such materials can be readily selected and employed by one of ordinary skill in the art. Further, one of ordinary skill in the art can readily select and employ means for suspending the present deformable continuous perfusion chamber in the major basin, whether such means are separate, integral, single or multi use, without undue experimentation. When using the additional means with the major basin and employing the present the deformable continuous perfusion chamber in-flow tubing is attached to the inlet port of the deformable chamber and out-flow tubing may or may not be attached to the outlet port of the deformable chamber. If out-flow tubing is not attached then sterile waste wash-out solution empties directly through the perforated means into the major basin. If out-flow tubing is used sterile waste wash-out solution travels through the tubing to a waste container located at a position lower than the continuous perfusion chamber, for example located on the floor.

Cryoprotective Agent As used herein, the term "cryoprotective agent" refers to one or more compounds including, for example, dimethylsulfoxide, glycerol, ethylene glycol, propylene glycol, butanediol, formamide, acetamide, polypropylene glycol, mannitol, trehalose, sorbitol, glucose, and sucrose, which may be used singly or in combination to protect cells and tissues from the damaging effects of freezing during cryopreservation.

Figure 3:
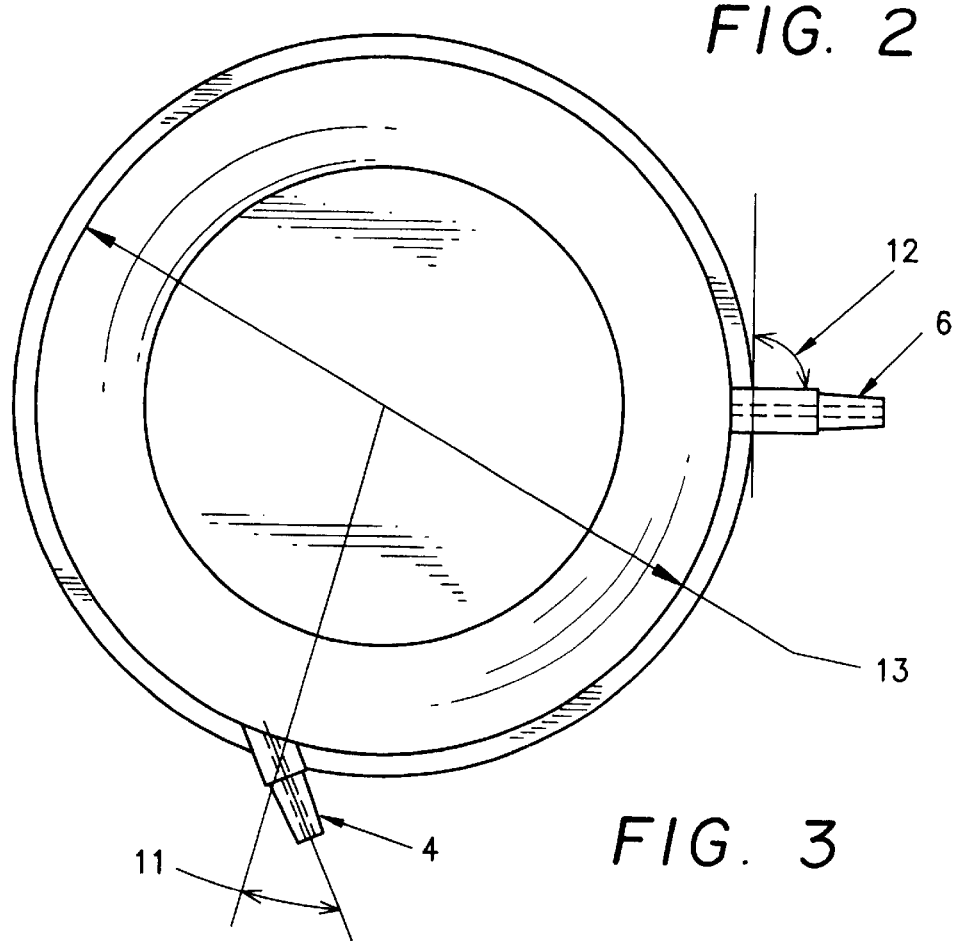
FIG. 3

Continuous-Multi-Step Dilution Process As used herein, the term "continuous-multi-step dilution process" refers to the process whereby the tissue to be treated is subjected to a continuous flow of wash-out solution such that the concentration of the cryoprotective agent in the tissue is reduced to levels demonstrated to be nontoxic to the tissue being treated and/or tissues and/or organisms into which the treated tissue is to be transplanted. In the present invention, the cryopreserved tissue is preferably added into the continuous perfusion chamber, or was cryopreserved in a deformable continuous perfusion chamber, and the continuous perfusion chamber is attached to a reservoir of wash-out solution via an inlet port. The wash-out solution is allowed to flow from the solution reservoir, into the chamber through the tissue (with or without stirring), and out of the continuous perfusion chamber via an outlet port, and into a waste container (FIG. 3). The waste container a sterile major basin where the sterile wash-out solution empties directly from the outlet port into the major basin, or the sterile wash-out waste solution may exit the outlet port, flow through out-flow tubing into a waste container located at a level lower than the continuous perfusion chamber, for example located on the floor.

Wash-out Solution By the term "wash-out solution" is intended a biocompatible solution which is preferably iso-osmotic or hyperosmotic to the tissue in its normal condition. Preferred wash-out solutions include for example, one or more of: Plasmalyte, Ringers solution, including LR5, Albuminar, tissue culture medium, citrated saline, phosphate buffered saline or similar commercially available clinically acceptable solution for use in washing tissues to which non-penetrating agents including for example, one or more of the following: mannitol, sucrose, sorbitol, polyethylene glycol, propanediol and/or trehalose, have been added to render the normally iso-osmolar solution hyperosmolar. The wash-out solution is most preferably a one-liter bag of a commercially available sterile solution. The volume of wash-out solution used is from 400 ml to 2,500 ml, preferably from 600 ml to 2,000 ml, more preferably from 750 to 1,500 ml and most preferably about 1,000 mls.

Figures 7, 8:
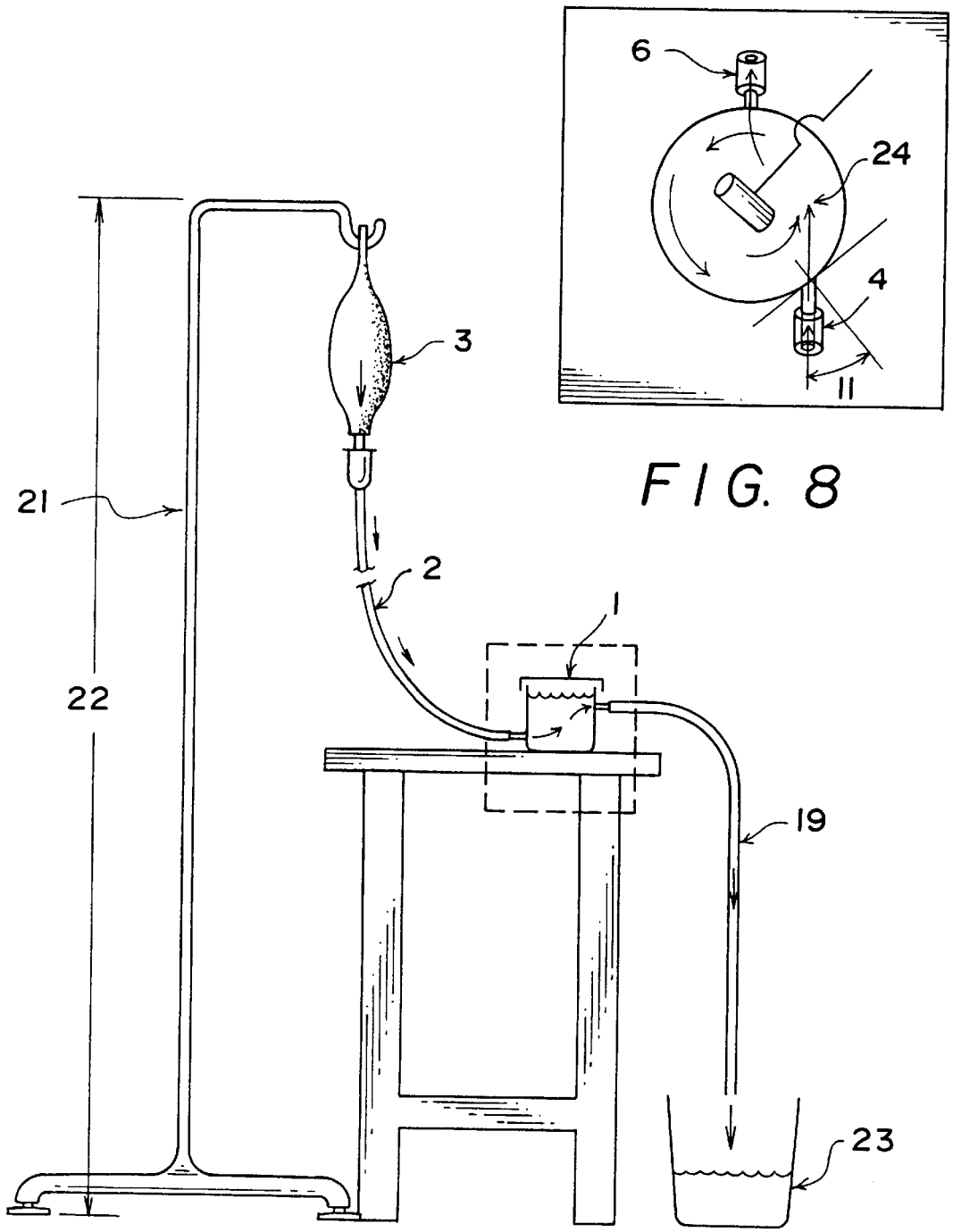
FIG. 7
FIG. 8

Stirring Effect. By the term "stirring effect" is intended for the purpose of the present invention the circular flow of wash-out solution through the present continuous perfusion chamber caused by the configuration of the inlet port and the outlet port relative to the chamber. For example, such circular flow can be achieved by providing the inlet port at an angle relative to the chamber as shown in FIG. 8.

Transition Period or Transition. By the term "transition period" or "transition" is intended for the purposes of the present invention a period of time where cryopreserved ultra cold tissue is exposed to room air (in its sterile container pouch) in order to allow the ultra cold tissue to slowly pass though the "glass" vitrified state ($-190°$ C. to approximately $-100°$ C.) to "ice" temperatures ($-100°$ C. to $0°$ C.). This period of time is generally from about three (3) minutes to about eleven (11) minutes, preferably from about five (5) minutes to about nine (9) minutes, and most preferably about seven (7) minutes.

Transition Temperature. By the term "transition temperature" is intended any known warming procedure which takes tissue from below its glass transition temperature to warmer than its glass transition temperature with the objective of reducing the potential for stress fracture formation.

Thawing. By the term "thawing" is intended any known thawing procedure which takes tissue from "amorphous glass"/"ice" temperatures to a thawed temperature (i.e., 0° C. to 40° C., preferably 27° C. to 37° C.). Generally, after the transition period, the frozen tissue is removed from its container using sterile technique and the frozen sterile tissue in its pouch is immediately placed into a large basin (preferably 2 to 5 liters) of preferably saline at preferably 37° C. to 42° C. Complete thawing generally takes about 4 to 8 minutes, preferably about 5 to 7 minutes. Thereafter the pouch is removed from the basin and processed. When using a simultaneous thaw/removal process, the tissue is thawed by subjecting it to a flow of wash-out solution at room temperature or warmed to an appropriate temperature, for example 37° C. to 42° C. or as otherwise readily determined by one of ordinary skill in the art.

II. Continuous-Multi-Step Dilution Process

A bag of wash-out solution is preferably suspended from a height of approximately 5 to 6 feet. The continuous perfusion chamber containing the tissue to be treated is located in a major basin or not in a major basin, on a bench or table (or similar appropriate surface) which is approximately 3 to 4 feet high, is attached to the solution reservoir via attached in-flow tubing, and wash-out solution is allowed to flow into the continuous perfusion chamber, through the chamber and around and through the tissue, and out of the chamber into a waste container. The dimensions of the tubing, design of the continuous perfusion chamber, operating height of the reservoir containing the wash-out solution, and location of the outlet port of the chamber or out-flow tubing leading into the waste container should be sufficient to allow the approximately one (1) liter of washout solution to drain into the waste container over a period of approximately 10 minutes. One of ordinary skill in the art to which the present invention pertains is readily able to determine and apply such parameters without undue experimentation. The inside diameter of the inlet port is preferably between 1.0 to 2.0 mm, more preferably between 1.2 to 1.7 mm, and most preferably about 1.5 mm. The inside diameter of the outlet port is always larger than the inside diameter of the inlet port preferably between 1.5 to 3.0 mm, more preferably between 1.5 to 2.55 mm, and most preferably about 2.0 mm. The continuous perfusion chamber design allows the operator to initiate the wash-out procedure and leave the system to operate without direct and continual monitoring. The rigid chamber is designed to retain the washed tissue in approximately 150–300 mls of solution, preferably about 250 mls of solution at the completion of the washing process and thus should the need for the tissue not coincide with completion of the washout procedure, the tissue can be allowed to remain for short periods of time, generally about $\leq 20$ minutes, as consistent with the need for cellular viability, matix structure, and/or matrix and cellular composition, in the chamber following completion of the procedure. Should the tissue need to be held for longer periods of time prior to transplantation it is desirable to hold the tissue at temperatures of from about 3° C. to about 10° C., more preferably from about 4° C. to about 6° C. This can be accomplished by placing the continuous perfusion chamber containing the sterile tissue in sterile wash-out solution in sterile slush. In the case where the process has been carried out using the continuous perfusion chamber in the major basin, sterile slush need only be added to the major basin. The addition of sterile slush to the basin will bring the temperature of the tissue within the acceptable range of from 3° C. to about 10° C. The tissue may then be held at this temperature for from about 30 minutes to about 2 hours prior to transplantation. In the case where the tissue has been processed using the present continuous-multi-step dilution process and the present continuous perfusion chamber where the perfusion chamber was not placed in the present major basin, the continuous perfusion chamber may be appropriately placed in the present sterile major basin containing sterile slush to achieve temperatures within the acceptable range in order to hold the tissue for the desired amount of time. One of ordinary skill in the art can readily determine how to aseptically place the present rigid or deformable continuous perfusion chamber in the present sterile major basin filled with sterile slush, without undue experimentation. Sterile slush is well known in the art to which the present invention pertains and is generally composed of frozen crushed sterile saline or equivalent.

The preferred wash-out solution possesses an osmotic pressure of from about 270 to 800 mOsm, but most preferably about 280 to 290 mOsm/KgH$_2$O (iso-osmotic) or 550–650 mOsm/KgH$_2$O (hyperosmotic). The wash-out solution can be any aqueous solution compatible with living human tissue but will preferably be a commercially available solution which is readily available in a hospital operating room environment, for example, (with or without nonpenetrating osmoticant isotonic saline, phosphate buffered saline, tissue culture medium, citrated saline, Albuminar®), Plasmalyte, Plasmalyte supplemented with mannitol and LR5 (Lactated Ringers 5, where various additives such as antibiotics, proteins, antiviral agents, osmoticants, permeation enhancers, and/or polysaccharides may be added to effect additional post-thawing viability of the tissue cell population.

The present continuous-multi-step dilution process is carried out at flow rates of from 25 to 500 mls/minute, preferably 50 to 250 mls/min and most preferably at a flow rate of from 75 to 150 mls/min. The tissue is preferably present in the continuous perfusion chamber in the medium used to cryopreserve the tissue, which according to current practice will involve a total volume of approximately 50 to 200 mls, preferably 75 to 150 mls, and most preferably about 100 mls where the tissue will approximate 3 to 30 mls, more preferably 10–20 mls. Alternatively, the tissue can be removed from the cryopreservation medium and placed in the chamber with wash-out solution, for example tissue culture medium. Typical cryopreservation medium includes medium supplemented with dimethylsulfoxide (10% final concentration) and fetal calf serum (10% final concentration). The wash-out solution preferably includes one or more of several commercially available iso-osmotic or hyperosmotic solutions including Plasmalyte, Ringers, Plasmalyte supplemented with mannitol, and LR5.

III. Continuous-multi-step Dilution Process: Removal of Cryoprotectant from Cryopreserved Tissue Following Thawing Using the Present Rigid Continuous Perfusion Chamber Cryopreserved human tissue is removed from ultra low temperature storage subjected to transition and thawed in its sterile packaging (pouch) according to standard protocol. While the tissue is being thawed, a one (1) liter bag of sterile wash-out solution is then hung from a standard "IV pole" (such as normally available in a hospital) and positioned next to a counter/table top. The presterilized room-temperature continuous perfusion chamber is placed onto a sterile field on the counter/table top. A waste basin is placed beneath the counter/table top and when the tissue is thawed, the pouch containing the tissue is aseptically opened and the tissue and liquid contents are gently poured into the continuous perfusion chamber. Alternatively, the tissue without the liquid contents may be aseptically placed into the chamber containing solution, for example tissue culture medium. The top of the continuous perfusion chamber is then replaced onto the chamber. The sterile in-flow tubing (the line attached to the inlet port positioned along the bottom of the chamber) is then inserted into the access port on the bag of wash--out solution such that wash-out solution begins to flow into the continuous perfusion chamber. While the chamber begins to fill, the outlet port line on the chamber is opened and the sterile out-flow tubing is placed such that it will drain into the waste container located beneath the counter/table. At this time, the approximate operating pressure of the system will be regulated by a wash-out solution height of 5 to 6 feet. The continuous-multi-step dilution procedure will require approximately 10 minutes and at the completion of the method, the tissue will remain in approximately 250 mls of wash-out solution at approximately room, i.e., ambient temperature. The osmolality of the solution exiting the continuous perfusion chamber versus time/volume will approximate a change from approximately 1800 to 3000 mOsm/KgH$_2$O to approximately 500–600 mOsm/KgH$_2$O when the wash-out solution is hyperosmotic, or to about 280–290 mOsm when the wash-out solution is iso-osmotic over the approximately 10 minutes (that illustrated in FIG. 7) and the final tissue concentration of cryoprotectant, for example dimethylsulfoxide will approximate 1.0 to 3.0%, more preferably below 3.0%, and most preferably about 2.0%. The tissue is then removed from the continuous perfusion chamber and is ready for transplantation.

Using the continuous perfusion chamber, the wash-out solution is allowed to fill the chamber to approximately 250 mls before the solution beings to exit the continuous perfusion chamber. After the chamber fills, perfusate flows to waste until such time as approximately 250 mls of wash-out solution remains covering the tissue. At this point, greater than 95% of the original solution used in cryopreserving the tissue will have been removed from the continuous perfusion chamber and the osmolality of the remaining solution will approximate that of the original wash-out solution, i.e. approximately 290 mOsm/kg water in the case of an iso-osmotic wash-out solution or approximately 550 mOsm/KgH$_2$O in the case of the hyperosmotic wash-out solution. In addition, following completion of the method, the tissue concentration of cryoprotectant (for example dimethylsulfoxide) is less than 3%.

IV. Continuous-multi-step Dilution Process: Removal of Cryoprotectant from Cryopreserved Tissue Simultaneously with Thawing Using a Deformable Continuous Perfusion Chamber Cryopreserved human tissue is removed from ultra low temperature storage and transition is initiated. A one (1) liter bag of wash-out solution is hung from a standard "IV pole" (such as is normally available in a hospital) and positioned next to a counter/table top. After transition, the continuous perfusion chamber which is the pouch that the tissue was cryopreserved in, having an inlet and an outlet, and allowed to lay "flat" on the table is placed onto a sterile field on the counter/table top, and simultaneous thawing and removal of cryoprotectant is effected when the sterile in-flow tubing (the line attached to the inlet port positioned along the seal of the chamber) is inserted into the access port on the bag of wash-out solution and sterile out-flow tubing can be attached to the outlet port on the chamber, and the outlet port positioned along the seal of the chamber and the out-flow tubing is opened and placed such that it will drain into the waste container for example, located beneath the counter/table. At this point those parts of the frozen liquid in the bag in close proximity to the bag are in a liquid state such that the wash-out solution begins to flow into, through, and out of the continuous perfusion chamber. While the chamber begins to flush, at this time, the approximate operating pressure of the system will be regulated by a wash-out solution height of 5 to 6 feet. The wash-out/thaw procedure will require approximately 9 to 10 minutes and at the completion of the method, the thawed tissue will be present in approximately 100 mls of iso-osmolar solution when the original wash-out solution is iso-osmotic, at approximately room, or ambient, temperature. The osmolality of the solution exiting the continuous perfusion chamber versus time/volume will change from approximately 1800–3000 mOsm/KgH$_2$O to approximately 280–290 mOsm/KgH$_2$O when the wash-out solution is iso-osmotic and 500–600 mOsm/KgH$_2$O when the wash-out solution is hyper-osmotic and the final tissue concentration of cryoprotectant will approximate less than 3.0%. The tissue is then removed from the continuous perfusion chamber and is ready for transplantation.

V. Continuous-multi-step Dilution Process: Removal of Cryoprotectant from Cryopreserved Tissue Simultaneous with Thawing Using the Present Rigid Continuous Perfusion Chamber Cryopreserved human tissue is removed from ultra low temperature storage and subjected to transition. A one (1) liter bag of wash-out solution is hung from a standard "IV pole" (such as is normally available in a hospital) and positioned next to a counter/table top. The presterilized or flash-sterilized, room-temperature continuous perfusion chamber placed onto a sterile field on the counter/table, is used to simultaneously effect tissue thawing and removal of cryoprotectant when the sterile in-flow tubing (the line attached to the inlet port positioned along the bottom of the chamber) is inserted into the access port on the bag of wash-out solution such that the solution begins to flow into, through, and out of the continuous perfusion chamber. The tissue after transition which is at an "ice" temperature, is then aseptically removed with its surrounding frozen liquid and placed in the continuous perfusion chamber. Alternatively, the tissue may be partially thawed and tissue with associated frozen solution may be aseptically placed into the chamber containing solution, for example washout solution. While the chamber begins to fill, the outlet port on the chamber is opened and the out-flow tubing is placed such that it will drain into the waste container located beneath the counter/table. At this time, the approximate operating pressure of the system will be regulated by a wash-out solution height of 5 to 6 feet. The wash-out/thaw procedure will require approximately 9 to 10 minutes and at the completion of the method, the thawed tissue will be present in approximately 250 mls of hyperosmolar solution when hyperosmolar wash-out solution is used and is at approximately room, or ambient temperature. The osmolality of the solution exiting the continuous perfusion chamber versus time/volume will approximate a change from approximately 3000 mOsm/KgH$_2$O to approximately 600 mOsm/KgH$_2$O (for example, as illustrated in Table 3) and the final tissue concentration of cryoprotectant will approximate less than 3.0%. The tissue is then removed from the continuous perfusion chamber and is ready for transplantation.

VI. Use of the Present Major Basin

A. Use of the Present Major Basin with the Present Rigid Continuous Perfusion Chamber, and without the Use of Out-flow Tubing The preferred embodiment of the present invention is performed using the present continuous-multi-step dilutional process and the present rigid continuous perfusion chamber placed in the present major basin.

In this embodiment cryopreserved human tissue is removed from ultra low temperature storage, transitioned, and then thawed in its sterile packaging (pouch). While the tissue is being thawed, a one (1) liter of sterile wash-out solution is then hung from standard "IV pole" (such as normally available in a hospital) and positioned next to a counter/table top. The sterile major basin is removed from its sterile packaging and placed onto a sterile field on the counter/table top. Next, the presterilized or flash-sterilized, room-temperature continuous perfusion chamber is placed onto a sterile field on the counter/table top and where sterile in-flow tubing is aseptically attached to the inlet port on the sterile chamber, and is placed in the sterile major basin. No out-flow tubing is attached to the outlet port on the rigid continuous perfusion chamber. The pouch containing the thawed sterile tissue is aseptically opened and the tissue and liquid contents are gently poured into the continuous perfusion chamber or the tissue itself is placed in the chamber containing wash-out solution or tissue culture medium. The top of the continuous perfusion chamber is then placed onto the chamber. The sterile in-flow tubing line attached to the inlet port of the continuous perfusion chamber is then aseptically inserted into the access port on the bag of wash-out solution such that the wash-out solution begins to flow into the continuous perfusion chamber. The outlet port on the chamber is opened and waste sterile wash-out solution will drain into the major basin. At this time, the approximate operating pressure of the system is regulated by a wash-out solution height of 5 to 6 feet. The continuous-multi-step solution procedure requires approximately 10 minutes and at the completion of the method, the tissue remains in approximately 250 mls of hyper-osmolar solution at approximately room temperature, if the original wash-out solution was hyper-osmotic. The final tissue concentration of cryoprotectant, for example dimethyl sulfoxide approximates about 1.0 to about 3.0%, more preferably below 3.0%, and most preferably about 2.0% or less. The tissue is then removed from the continuous perfusion chamber and is ready for transplantation.

The processed tissue may be held in the continuous perfusion chamber containing approximately 250 mls of wash-out solution for periods of up to about 15 minutes at room temperature. Should it be necessary to hold the tissue for longer periods of time, sterile slush may be added to the major basin to cool the tissue to a temperature of from about 2° C. to about 10° C., more preferably from about 4° C. to about 6° C. The tissue may be held at these temperatures for periods of time of from about 30 minutes to about 2 hours without any detrimental effect to cell viability.

Alternatively, the above procedure may be performed using sterile out-flow tubing aseptically attached to the outlet port of the rigid continuous perfusion chamber, and the chamber may then be placed in the major basin. In this embodiment the out-flow tubing runs from the outlet port up over the lip of the major basin and down to a waste container at a level lower than the major basin, for example the waste container can be located on the floor.

Using the major basin and the rigid continuous perfusion chamber either with the use of out-flow tubing or without the use of out-flow tubing, tissue may be prepared either after thawing as described, or simultaneously with thawing as described above. When the tissue is prepared simultaneously with thawing, the tissue in the pouch is also subjected to a transition period. After transition the tissue and the surrounding frozen cryosolution are at "ice" temperatures, for example, at temperatures of from approximately about −110° C. to −90° C.

A Using the Major Basin with the Present Deformable Continuous Perfusion Chamber In this embodiment tissue is processed in the deformable continuous perfusion chamber which is the pouch in which the tissue is initially cryopreserved where in the pouch/deformable chamber has an inlet port and an outlet port which at the time of cryopreservation are sealed for example, with a septum. Using the deformable continuous perfusion chamber is advantageous in that it minimizes tissue handling by personnel. In this embodiment the pouch/deformable continuous perfusion chamber containing tissue and liquid is subjected to transition alone (simultaneous thaw/removal or cryoprotectant) or transition and thawing. Thereafter sterile in-flow tubing is aseptically attached to the inlet port of the chamber which attachment breaks the seal (septum) between the inlet port and the pouch/chamber. Out-flow tubing may or may not be attached to the out-flow port. If out-flow tubing is not attached to the outlet port, the seal between the outlet port and the pouch must be aseptically broken, for example by insertion of a sterile outlet connector. The deformable continuous perfusion chamber is then placed in the sterile major basin using means to suspend the continuous perfusion chamber in the major basin to a point sufficient such that waste wash-out fluid exiting the outlet port when out-flow tubing is not used, is at a level below the outlet port. Such means can be readily selected and employed by one of ordinary skill in the art without undue experimentation. Such means may be separate from the major basin or may be integrally formed with the major basin. Such means may include a perforated shallow insert to be placed in the major basin, a screen or rack to be placed in the major basin or on top of the major basin or across the major basin, such means may also include means integrally formed with the cryopreservation pouch/deformable perfusion chamber having an inlet port and outlet port.

VII. Preferred Clinical Protocol

Figure 14:
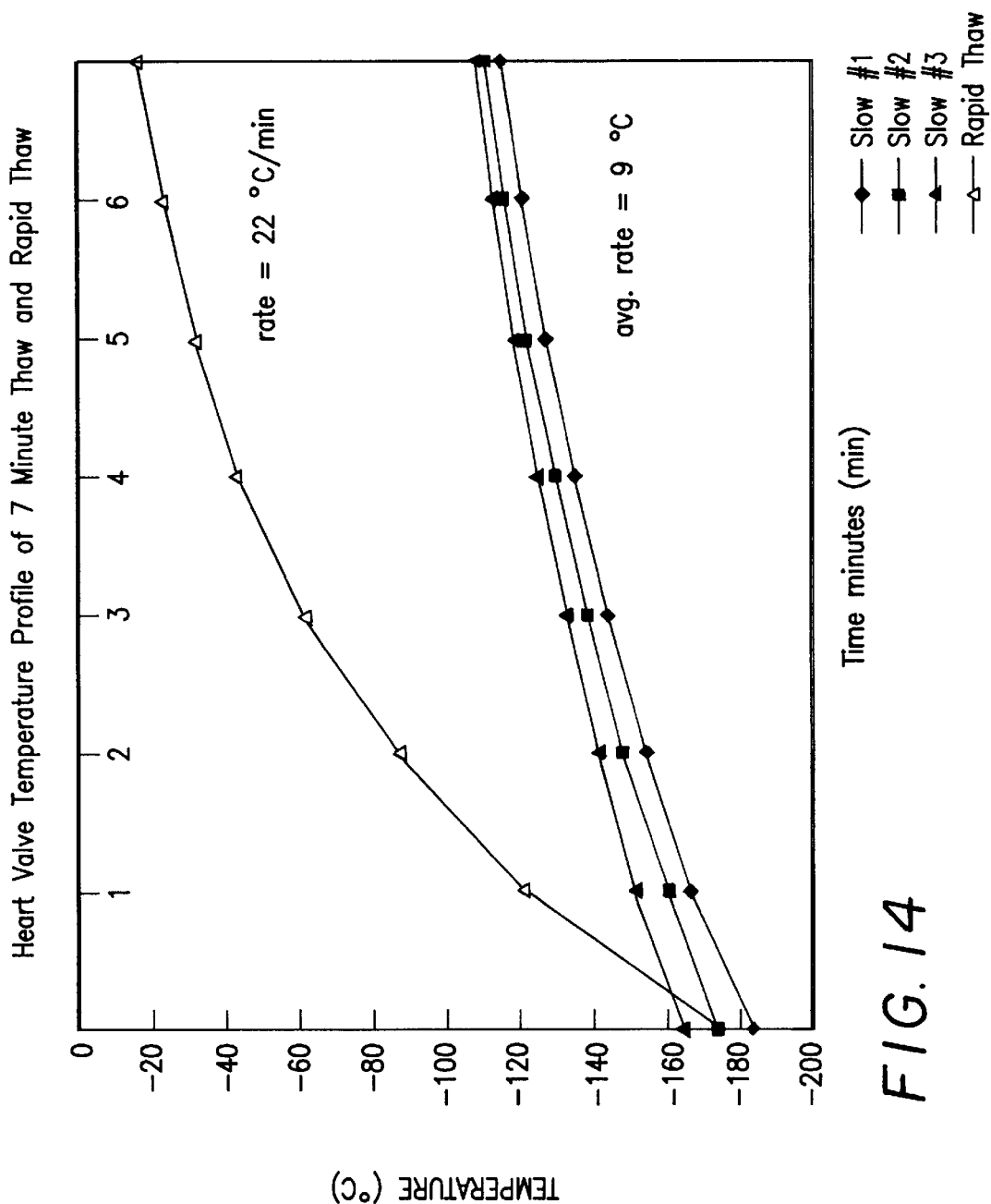
FIG. 14

In the O.R. suite, the graft is removed from cryogenic storage (a freezer or a cryoshipper at sites where storage freezers are not utilized) and placed on a non-sterile table with the box lid open and the pouch completely removed from the CryoTainer for a period of seven (7) minutes. This exposure to room air will allow the ultracold tissue to slowly transition through the "glass" vitrified state (−190° C. to approximately −100° C.) to "ice" temperatures (−100° C. to 0° C.) (See FIG. 14).

At the end of the seven (7) minute room air exposure period, the graft is removed from the box by an O.R. circulator who then, utilizing sterile technique, peels open the outer bag. The frozen graft in the inner sterile bag is delivered to a scrub nurse or O.R. tech. The graft (while still in the sterile bag) is then immediately placed into a large sterile basin (approximately 3–4 liters) of sterile 37—42° iso-osmotic saline.

Once the graft has completely thawed (approximately 5–7 minutes), the scrub nurse/technician removes the bag from the saline bath, opens the pouch and empties entire thawed contents (tissue plus cryosolution) into the continuous perfusion chamber. This sterile custom continuous perfusion chamber, provided by LifeNet, and a basin will be provided with each graft. A loose-fitting lid is then placed onto the basin.

The scrub nurse/technician then attaches an IV line to the in-flow port. The continuous perfusion chamber is then placed into the major basin.

The spiked proximal end of the in-flow line is then handed off the operative field to a circulator.

The circulator then inserts the spiked end of the in-flow line into a one (1) liter bag of wash-solution. The wash-solution is allowed to flow at a fully open rate into the graft containing receptacle on the operative field. As the wash-solution flows into the receptacle, the diluted cryosolution freely flows into the major basin. Preferably the wash-solution will be Plasmalyte (an iso-osmotic electrolyte) amended with a mannitol additive (an extracellular nonpenetrating osmoticant) or LR5.

After approximately 9–10 minutes, the one (1) liter bag will have emptied. The graft is now ready for implantation. If the operative procedure is delayed, the tissue is to stay in the remaining wash-solution/cryoprotectant bath until implantation. Approximately 250 mls of final solution will remain in the receptacle due to the in-flow, out-flow port height difference.

This procedure reduces the level of residual cryoprotectant, for example DMSO in the tissue to approximately 2%.

The following examples illustrate the present process.

EXAMPLES

Example 1

Figure 9:
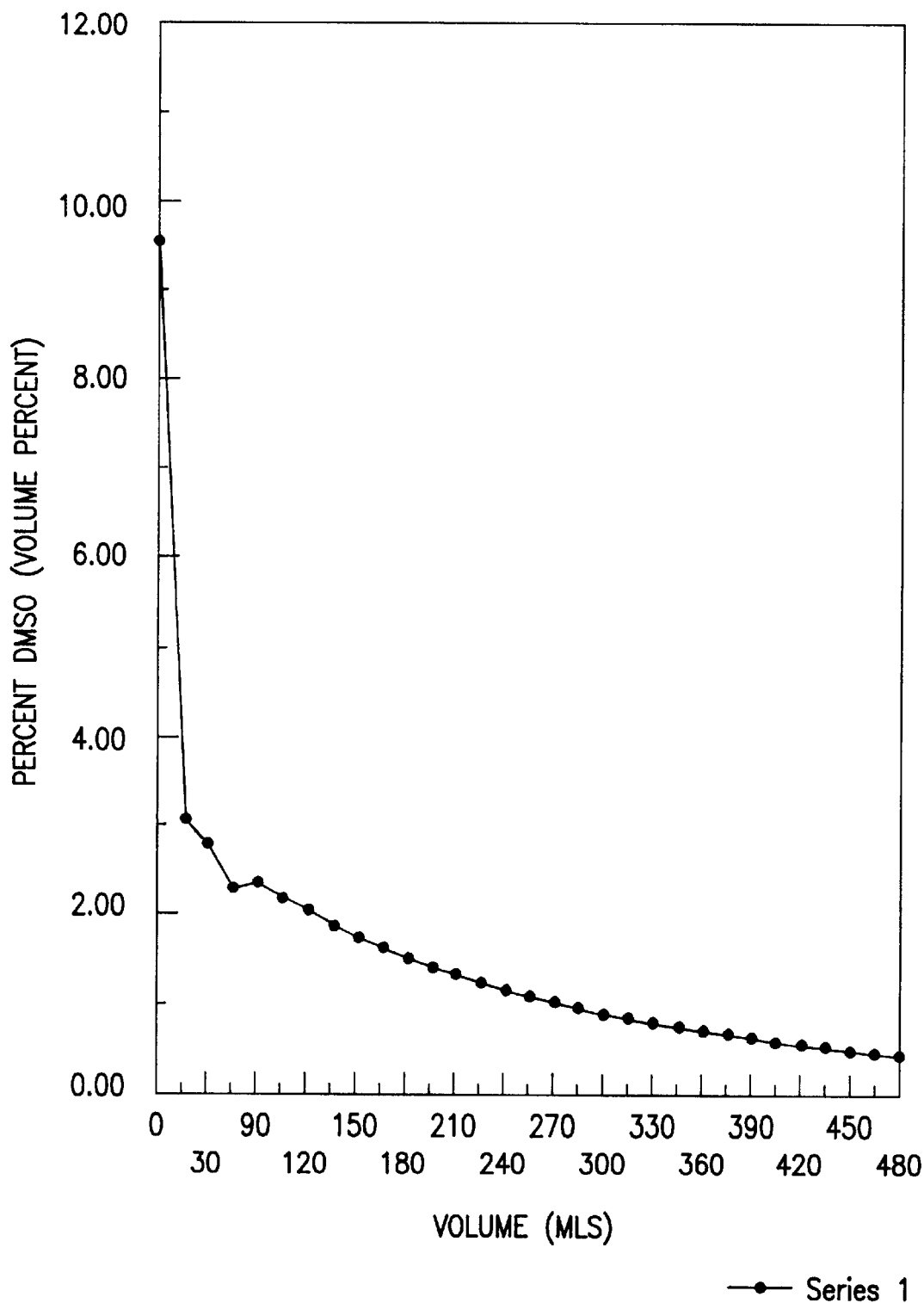
FIG. 9

A cryopreserved human heart valve was removed from storage in an ultra low temperature storage container, transitioned and thawed (see FIGS. 1 and 7). While the valve was being thawed, a one (1) liter bag of a Plasmalyte is hung from a standard "IV pole" 21 (such as, normally available in a hospital) and positioned next to a counter/table top. The continuous perfusion chamber 1 was removed from its' sterile packaging and placed onto a sterile field on the counter/table top. (See attached FIG. 14 for temperature profile data during transitioning). A waste basin 23 was placed beneath the counter/table top and when the valve was thawed, the pouch containing the valve was aseptically opened and the valve and liquid contents were gently poured into the continuous perfusion chamber. The top of the continuous perfusion chamber was then replaced onto the chamber and closed to form a loose seal. The in-flow line 2 (the line attached to the inlet port positioned along the bottom of the chamber) was then inserted into the access port on the bag 3 of Plasmalyte such that Plasmalyte began to flow into the continuous perfusion chamber. While the chamber began to fill, the outlet port line 19 on the chamber was opened and placed such that it drained into the waste basin 23 located beneath the counter/table. At that time, the approximate operating pressure of the system was regulated by a wash-out solution height of 5 to 6 feet. The wash-out procedure required approximately 10 minutes and at the completion of the method, the valve remained in approximately 250 mls. of iso-osmolar solution at approximately room, ambient temperature. The osmolality of the solution exiting the continuous perfusion chamber versus time/volume changed from an approximated 3000 mOsm/KgH$_2$O to approximated 280–290 mOsm/KgH$_2$O, the concentration of DMSO in the washout solution changed from approximately 10% to approximately 0.05% (see FIG. 9) and the final tissue concentration of dimethyl sulfoxide approximated 2.1% to 2.7%. The valve was then removed from the continuous perfusion chamber and was ready for transplantation.

With the continuous perfusion chamber illustrated in FIG. 1, the wash-out solution was allowed to fill the chamber to approximately 250 mls. before solution began to exit the continuous perfusion chamber. After the chamber filled, perfusate was allowed to flow to waste until such time as approximately 250 mls. of wash-out solution remained covering the tissue. At that point, greater than 95% of the original solution used in freezing the tissue had been removed from the continuous perfusion chamber and the osmolality of the remaining solution approximated that of the original wash-out solution, i.e. approximately 290 to 320 mOsm/KgH$_2$O. In addition, following completion of the method, the tissue concentration of dimethylsulfoxide was less than 3.0%.

Example 2

A cryopreserved human heart valve was removed from storage in an ultra low temperature storage container, transitioned and thawed (see FIGS. 1 and 7). While the valve was being thawed, a one (1) liter bag of Plasmalyte supplemented with sterile liquid mannitol to an approximate osmolality of 600 mOsm/KgH$_2$O was hung from a standard "IV pole" 21 (such is normally available in a hospital) and positioned next to a counter/table top. The continuous perfusion chamber 1 was removed from its' sterile packaging and placed onto a sterile field on the counter/table top. A waste basin 23 was placed beneath the counter/table top and the valve was thawed, the pouch containing the valve was aseptically opened and the valve was carefully grasped near the distal end of the conduit using a suitable sterile tissue holding device and transferred from the liquid freezing solution into the continuous perfusion chamber to which had been added 100 mls. of Plasmalyte supplemented with mannitol without cryoprotective agent. The top of the continuous perfusion chamber was then replaced onto the chamber. The inlet line 2 (the line attached to the inlet port positioned along the bottom of the chamber) was then inserted into the access port on the bag 3 of Plasmalyte supplemented with mannitol such that the Plasmalyte solution began to flow into the continuous perfusion chamber. While the chamber began to fill, the outlet port line 19 on the chamber was opened and placed such that is drained into the waste basin 23 located beneath the counter/table. At that time, the approximate operation pressure of the system was regulated by a wash-out solution height 22 of 5 to 6 feet. The wash-out procedure required approximately 10 minutes and at the completion of the method, the valve remained in approximately 250 mls. of hyper-osmolar solution at approximately room, or ambient temperature. The osmolality of the solution exiting the continuous perfusion chamber versus time/volume approximated a change from approximately 900 mOsm/KgH$_2$O to approximately 600 mOsm/KgH$_2$O and the final tissue concentration of dimethyl sulfoxide approximated 1.5 to 2.5%. The valve was then removed from the continuous perfusion chamber and was ready for transplantation.

Example 3

A cryopreserved human heart valve was removed from storage in an ultra low temperature storage container, transitioned and thawed (See FIGS. 1 and 7). A one (1) liter bag of LR5 was hung from a standard "IV pole" 21 (such as is normally available in a hospital) and positioned next to a counter/table top. The continuous perfusion chamber 1 was removed from its' sterile packaging and placed onto a sterile field on the counter/table top. A waste basin 23 was placed beneath the counter/table top and when the valve was thawed, the pouch containing the valve was aseptically opened and the valve and cryopreservation solution carefully transferred into the continuous perfusion chamber 1. The top of the continuous perfusion chamber was then replaced onto the chamber. The in-flow line 2 (the line attached to the inlet port positioned along the bottom of the chamber) was then inserted into the access port on the bag of LR5 such that LR5 began to flow into the continuous perfusion chamber. While the chamber began to fill, the outlet port line 19 on the chamber was opened and placed such that it drained into the waste basin 23 located beneath the counter/table. At that time, the approximate operating pressure of the system was regulated by a wash-out solution height 22 5 to 6 feet. The wash-out procedure required approximately 10 minutes and at the completion of the method, the valve remained in approximately 250 mls. of hyperosmolar solution at approximately room, or ambient temperature. The osmolality of the solution exiting the continuous perfusion chamber versus time/volume approximated a change from approximately 3000 mOsm/KgH$_2$O to approximately 600 mOsm/KgH$_2$O (see FIG. 10 and Table 1) and the DMSO concentration in the washout solution changed from approximately 10% to approximately 0.2% (see FIG. 9 and Table 2) and the final tissue concentration of dimethyl sulfoxide approximated 1.5 to 2.5% (see Table 3). The valve was then removed from the continuous perfusion chamber and was ready for transplantation.

TABLE 1

OSMOLALITY OF WASH-OUT SOLUTION
VALVE C

| VOLUME | mOSM/L | VOLUME | mOSM/L |
|---|---|---|---|
| 0 | 3063.2 | 545 | 667.0 |
| 95 | 878.0 | 560 | 661.4 |
| 110 | 894.2 | 575 | 654.8 |
| 125 | 869.0 | 590 | 652.4 |
| 140 | 864.6 | 605 | 644.4 |
| 155 | 866.4 | 620 | 634.2 |
| 170 | 856.2 | 635 | 632.0 |
| 185 | 837.0 | 650 | 630.0 |
| 200 | 827.2 | 665 | 628.8 |
| 215 | 818.2 | 680 | 629.2 |
| 230 | 812.2 | 695 | 622.2 |
| 245 | 798.0 | 710 | 621.0 |
| 260 | 794.2 | 725 | 617.6 |
| 275 | 784.0 | 740 | 612.8 |
| 290 | 783.8 | 755 | 619.0 |
| 305 | 778.8 | 770 | 620.4 |
| 320 | 769.0 | 785 | 620.0 |
| 335 | 760.0 | 800 | 620.0 |
| 350 | 756.0 | 815 | 619.4 |
| 365 | 748.2 | 830 | 614.8 |
| 380 | 739.4 | 845 | 611.6 |
| 395 | 724.8 | 860 | 613.2 |
| 410 | 716.4 | 875 | 608.6 |
| 425 | 708.6 | 890 | 610.0 |
| 440 | 701.4 | 905 | 607.2 |
| 455 | 699.4 | 920 | 606.0 |
| 470 | 693.6 | 935 | 603.8 |
| 485 | 688.6 | 950 | 604.2 |
| 500 | 680.6 | 965 | 606.0 |
| 515 | 673.6 | 980 | 614.0 |
| 530 | 675.6 | | |

TABLE 2

DMSO CONCENTRATION OF WASH-OUT SOLUTION
(PLASMALYTE & 7.14% MANNITOL)
VALVE C

| VOLUME | % DMSO | VOLUME | % DMSO |
|---|---|---|---|
| 0 | 10.202149600 | 545 | 0.452936706 |
| 95 | 1.598306373 | 560 | 0.422538269 |
| 110 | 1.686244707 | 575 | 0.386711541 |

TABLE 2-continued

DMSO CONCENTRATION OF WASH-OUT SOLUTION
(PLASMALYTE & 7.14% MANNITOL)
VALVE C

| VOLUME | % DMSO | VOLUME | % DMSO |
|---|---|---|---|
| 125 | 1.549451742 | 590 | 0.373683639 |
| 140 | 1.525567257 | 605 | 0.330257301 |
| 155 | 1.535338183 | 620 | 0.274888720 |
| 170 | 1.479969602 | 635 | 0.262946477 |
| 185 | 1.375746390 | 650 | 0.252089893 |
| 200 | 1.322549126 | 665 | 0.245575942 |
| 215 | 1.273694496 | 680 | 0.247747259 |
| 230 | 1.241124742 | 695 | 0.209749213 |
| 245 | 1.164042992 | 710 | 0.203235262 |
| 260 | 1.143415481 | 725 | 0.184779069 |
| 275 | 1.088046900 | 740 | 0.158723266 |
| 290 | 1.086961242 | 755 | 0.192378678 |
| 305 | 1.059819781 | 770 | 0.199978287 |
| 320 | 1.006622517 | 785 | 0.197806970 |
| 335 | 0.957767886 | 800 | 0.197806970 |
| 350 | 0.936054717 | 815 | 0.194549995 |
| 365 | 0.893714038 | 830 | 0.169579850 |
| 380 | 0.845945066 | 845 | 0.152209315 |
| 395 | 0.766691999 | 860 | 0.160894583 |
| 410 | 0.721094344 | 875 | 0.135924438 |
| 425 | 0.678753664 | 890 | 0.143524047 |
| 440 | 0.639669960 | 905 | 0.128324829 |
| 455 | 0.628813375 | 920 | 0.121810878 |
| 470 | 0.597329280 | 935 | 0.109868635 |
| 485 | 0.570187819 | 950 | 0.112039952 |
| 500 | 0.526761481 | 965 | 0.121810878 |
| 515 | 0.488763435 | 980 | 0.165237216 |
| 530 | 0.499620020 | | |

TABLE 3

DMSO CONCENTRATION IN TISSUE
(STAINLESS STEEL CONTINUOUS PROFUSION CHAMBER)

| | PEAK AREA | % DMSO | DILUTION | FINAL (% DMSO) |
|---|---|---|---|---|
| VALVE A | 19711 | 0.203740963 | 11.04784689 | 2.250899 |
| VALVE B | 22669 | 0.235705433 | 8.128309572 | 1.915887 |
| VALVE C | 24930 | 0.259058046 | 10.96818664 | 2.841397 |
| | | | AVERAGE = | 2.336061 |

Figure 10:
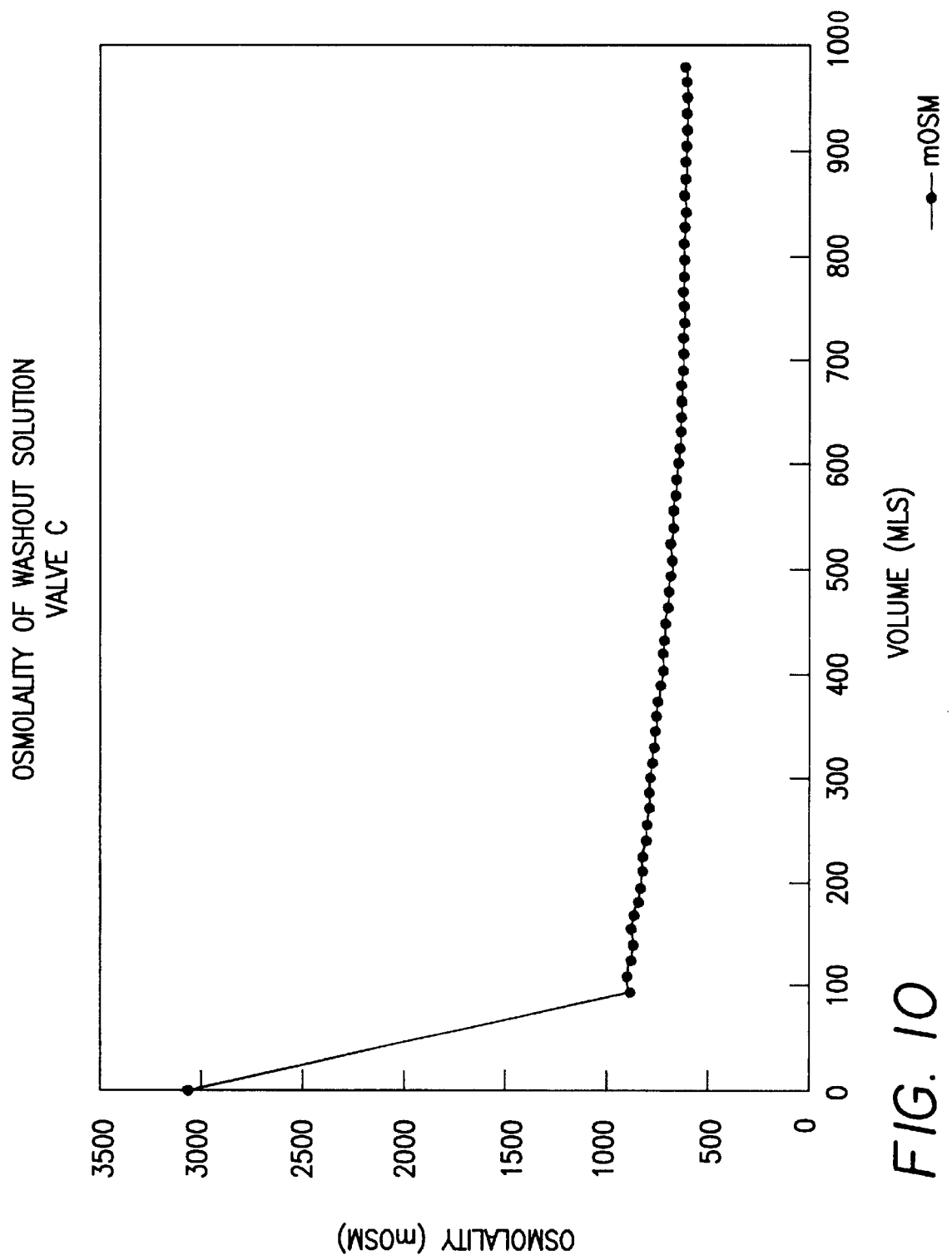
FIG. 10
Figure 11:
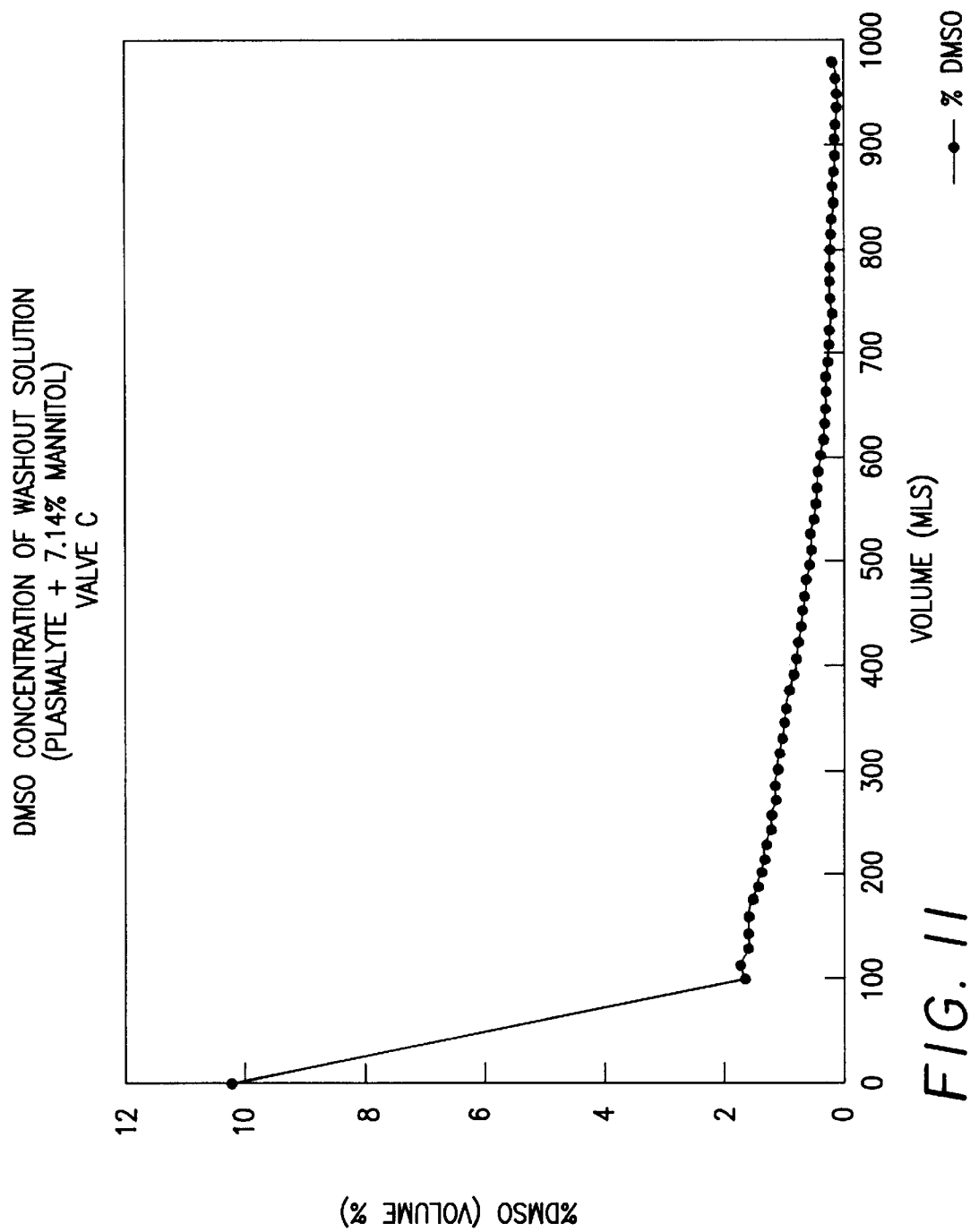
FIG. 11

The heart valve used in the wash-out procedures described in example 3 and FIGS. 10 and 11 were minced and extracted in 10% methanol in ultra pure water. The extract was then analyzed using reverse-phase high performance liquid chromatography and the tissue DMSO concentrations calculated as a volume percent. The results of three (3) separate wash-out procedures were used to calculate a mean and standard deviation for tissue concentrations of DMSO in heart valves processed using the continuous perfusion chamber with Plasmalyte supplemented with 7.14% mannitol as the wash-out solution.

Example 4

Figure 2:
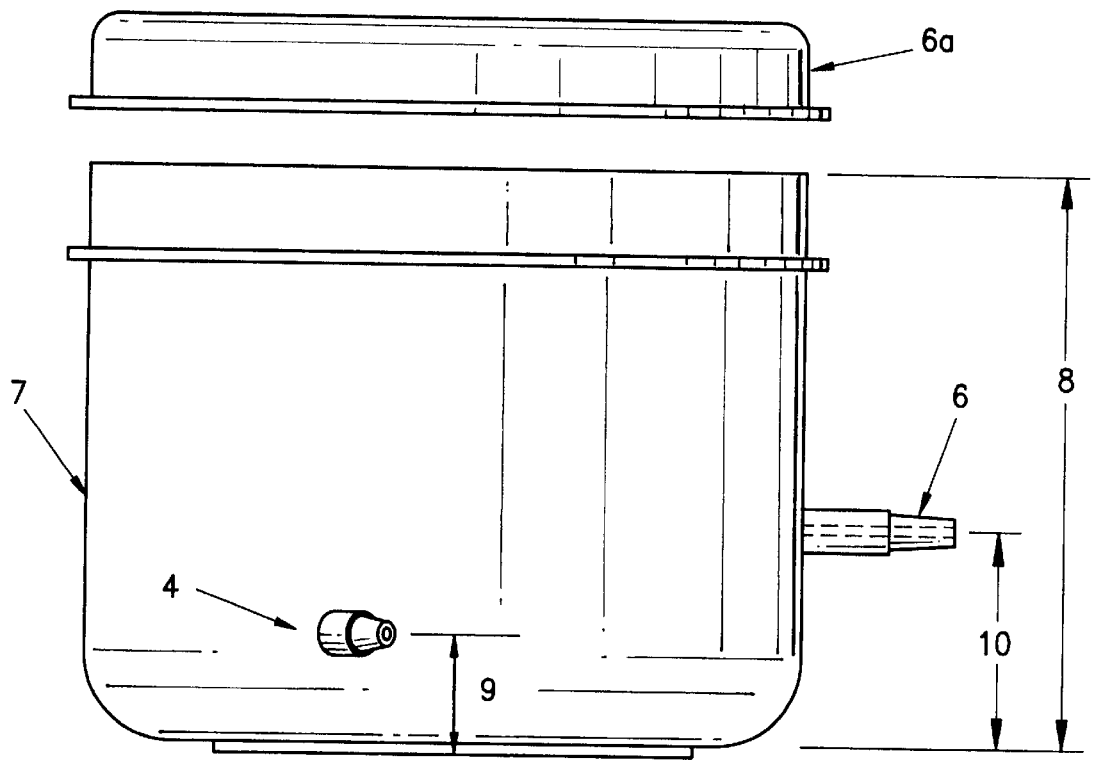
FIG. 2

A cryopreserved human heart valve is removed from storage in an ultra low temperature storage container such as illustrated in FIG. 2 and subjected to transition. As illustrated in FIG 7, a one (1) liter bag of saline was hung from a standard "IV pole " 21 (such as is normally available in a hospital) and positioned next to a counter/table top. The continuous perfusion chamber 1 was removed from its' sterile packaging and placed onto a sterile field on the counter/table top. The transitioned tissue/frozen cryosolution at an ice temperature was then gently removed from its pouch and placed into the chamber 1 using sterile technique.

Tissue thawing and removal of cryoprotectant were simultaneously effected when the inlet line 2 (the line attached to the inlet port positioned along the bottom of the chamber) was inserted into the access port on the bag of saline such that saline began to flow into, through, and out of the continuous perfusion chamber. While the chamber began to fill, the outlet port line 19 on the chamber was opened and placed such that it drained into the waste basin 23 located beneath the counter/table. At that time, the approximate operating pressure of the system was regulated by a wash-out solution height 22 of 5 to 6 feet. The wash-out/thaw procedure required approximately 9 to 10 minutes and at the completion of the method, the thawed tissue was present in approximately 250 mls of iso-osmolar solution at approximately room, or ambient temperature. The osmolality of the solution exiting the continuous perfusion chamber versus time/volume approximated a change from approximately 3000 mOsm/KgH$_2$O to approximately 280–290 mOsm/KgH$_2$O and the final tissue concentration of dimethyl sulfoxide approximated less than 3.0%. The valve was then removed from the continuous perfusion chamber and was ready for transplantation.

Example 5

As illustrated in FIG. 7, a cryopreserved human heart valve is removed from storage in an ultra low temperature storage container, transitioned and thawed. A one (1) liter bag of LR5 was hung from a standard "IV pole" (21 such as is normally available in a hospital) and positioned next to a counter/table top. The continuous perfusion chamber 1 was removed from its' sterile packaging and placed onto a sterile field on the counter/table top. A waste basin 23 was placed beneath the counter/table top and when the valve was thawed, the pouch containing the valve was aseptically opened and the valve and liquid contents were gently poured into the continuous perfusion chamber 1. The top of the continuous perfusion chamber was then replaced onto the chamber. The in-flow line 2 (the line attached to the inlet port positioned along the bottom of the chamber) was then inserted into the access port on the bag of LR5 such that LR5 began to flow into the continuous perfusion chamber. While the chamber began to fill, the outlet port line 19 on the chamber was opened and placed such that it drained into the waste basin 23 located beneath the counter/table. At that time, the approximate operating pressure of the system was regulated by a wash-out solution height 22 5 to 6 feet. The wash-out procedure required approximately 10 minutes and at the completion of the method, the valve remained in approximately 250 mls of hyperosmolar solution at approximately room, or ambient temperature. The osmolality of the solution exiting the continuous perfusion chamber versus time/volume approximated that illustrated in FIG. 12 (Table 4), and the DMSO concentration in the washout solution approximated that illustrated in FIG. 13 (Table 5) and the final tissue concentration of dimethylsulfoxide approximated 2.0 to 3.0% (Table 6). The valve was then removed from the continuous perfusion chamber and was ready for transplantation.

TABLE 4

VALVE A
OSMOLALITY OF SOLUTION EXITING
CONTINUOUS PERFUSION CHAMBER

| VOLUME | mOsm/kg H$_2$O | mOsm/kg H$_2$O | mOsm/kg H$_2$O | AVERAGE | STD DEVIATION |
|---|---|---|---|---|---|
| 0 | 2069 | 2071 | 2068 | 2069.33333 | 1.527525 |
| 15.0 | 843 | 844 | 844 | 843.666667 | 0.577350 |
| 30.0 | 838 | 841 | 840 | 839.666667 | 1.527525 |
| 45.0 | 828 | 829 | 829 | 828.666667 | 0.577350 |
| 60.0 | 817 | 820 | 815 | 817.333333 | 2.516611 |
| 75.0 | 803 | 803 | 803 | 803.000000 | 0 |
| 90.0 | 788 | 789 | 789 | 788.666667 | 0.577350 |
| 105.0 | 777 | 773 | 775 | 775.000000 | 2.000000 |
| 119.0 | 763 | 766 | 763 | 764.000000 | 1.732051 |
| 132.5 | 750 | 755 | 754 | 753.000000 | 2.645751 |
| 146.5 | 741 | 740 | 741 | 740.666667 | 0.577350 |
| 161.0 | 730 | 731 | 731 | 730.666667 | 0.577350 |
| 175.0 | 720 | 722 | 724 | 722.000000 | 2.000000 |
| 189.0 | 711 | 712 | 713 | 712.000000 | 1.000000 |
| 203.5 | 703 | 701 | 704 | 702.666667 | 1.527525 |
| 217.5 | 693 | 698 | 693 | 694.666667 | 2.886751 |
| 231.5 | 686 | 689 | 689 | 688.000000 | 1.732051 |
| 245.5 | 674 | 678 | 678 | 676.666667 | 2.309401 |
| 259.0 | 671 | 671 | 673 | 671.666667 | 1.154701 |
| 272.5 | 666 | 664 | 666 | 665.333333 | 1.154701 |
| 285.5 | 659 | 660 | 663 | 660.666667 | 2.081666 |
| 299.5 | 651 | 651 | 651 | 651.000000 | 0 |
| 313.5 | 648 | 647 | 647 | 647.333333 | 0.577350 |
| 327.5 | 643 | 643 | 642 | 642.666667 | 0.577350 |
| 341.0 | 638 | 638 | 637 | 637.666667 | 0.577350 |
| 355.0 | 632 | 632 | 633 | 632.333333 | 0.577350 |
| 368.5 | 626 | 631 | 626 | 627.666667 | 2.886751 |
| 382.5 | 625 | 623 | 627 | 625.000000 | 2.000000 |
| 396.5 | 616 | 617 | 618 | 617.000000 | 1.000000 |
| 410.5 | 615 | 615 | 617 | 615.666667 | 1.154701 |
| 425.5 | 611 | 610 | 613 | 611.333333 | 1.527525 |
| 439.5 | 610 | 605 | 609 | 608.000000 | 2.645751 |
| 454.0 | 602 | 602 | 603 | 602.333333 | 0.577350 |
| 467.5 | 607 | 609 | 606 | 607.333333 | 1.527525 |
| 481.5 | 603 | 605 | 606 | 604.666667 | 1.527525 |
| 494.5 | 602 | 600 | 600 | 600.666667 | 1.154701 |
| 509.0 | 597 | 596 | 599 | 597.333333 | 1.527525 |
| 523.0 | 599 | 596 | 596 | 597.000000 | 1.732051 |
| 536.0 | 593 | 594 | 591 | 592.666667 | 1.527525 |
| 550.0 | 592 | 594 | 591 | 592.333333 | 1.527525 |
| 563.5 | 591 | 587 | 586 | 588.000000 | 2.645751 |
| 577.0 | 588 | 585 | 585 | 586.000000 | 1.732051 |
| 591.5 | 586 | 584 | 586 | 585.333333 | 1.154701 |
| 605.0 | 580 | 580 | 579 | 579.666667 | 0.577350 |
| 618.5 | 581 | 578 | 578 | 579.000000 | 1.732051 |
| 632.0 | 577 | 582 | 580 | 579.666667 | 2.516611 |
| 645.5 | 577 | 573 | 576 | 575.333333 | 2.081666 |
| 658.5 | 575 | 575 | 572 | 574.000000 | 1.732051 |
| 672.0 | 565 | 563 | 560 | 562.666667 | 2.516611 |
| 686.0 | 560 | 558 | 565 | 561.000000 | 3.605551 |
| 700.5 | 563 | 561 | 563 | 563.333333 | 0.577350 |
| 714.5 | 565 | 570 | 571 | 568.666667 | 3.214550 |
| 729.0 | 563 | 566 | 567 | 565.333333 | 2.081666 |
| 742.0 | 570 | 568 | 565 | 567.666667 | 2.516611 |
| 755.0 | 564 | 560 | 566 | 563.333333 | 3.055050 |
| 768.5 | 564 | 570 | 570 | 568.000000 | 3.464102 |
| 782.5 | 567 | 562 | 567 | 565.333333 | 2.886751 |
| 797.0 | 562 | 565 | 560 | 562.333333 | 2.516611 |
| 810.5 | 559 | 563 | 566 | 562.666667 | 3.511885 |
| 824.0 | 565 | 559 | 563 | 562.333333 | 3.055050 |
| 837.5 | 562 | 560 | 564 | 562.000000 | 2.000000 |
| 851.0 | 562 | 563 | 562 | 562.333333 | 0.577350 |
| 863.5 | 561 | 561 | 562 | 561.333333 | 0.577350 |
| 873.0 | 560 | 565 | 560 | 561.666667 | 2.886751 |

TABLE 5

VALVE A
DMSO CONCENTRATION IN WASH-OUT SOLUTION

| VOLUME | % DMSO | VOLUME | % DMSO |
|---|---|---|---|
| 0 | 7.993297 | 534 | 0.798594 |
| 95 | 1.982181 | 547.5 | 0.823116 |
| 110 | 1.962563 | 561.5 | 0.810038 |
| 125 | 1.908615 | 574.5 | 0.79042 |
| 140 | 1.853033 | 589 | 0.744072 |
| 155 | 1.782737 | 603 | 0.772437 |
| 170 | 1.712441 | 616 | 0.751185 |
| 185 | 1.645414 | 630 | 0.74955 |
| 199 | 1.591466 | 643.5 | 0.728298 |
| 212.5 | 1.537518 | 657 | 0.718489 |
| 226.5 | 1.477031 | 671 | 0.71522 |
| 241 | 1.427988 | 685 | 0.687428 |
| 255 | 1.385483 | 698.5 | 0.684159 |
| 269 | 1.336439 | 712 | 0.687428 |
| 283.5 | 1.290665 | 725.5 | 0.666176 |
| 297.5 | 1.25143 | 738.5 | 0.659637 |
| 311.5 | 1.218735 | 752 | 0.604054 |
| 325.5 | 1.163152 | 766 | 0.59588 |
| 339 | 1.13863 | 780.5 | 0.607324 |
| 352.5 | 1.107569 | 794.5 | 0.63348 |
| 365.5 | 1.084682 | 809 | 0.617133 |
| 379.5 | 1.037273 | 822 | 0.628576 |
| 393.5 | 1.019291 | 835 | 0.443845 |
| 407.5 | 0.996403 | 848.5 | 0.630211 |
| 421 | 0.971882 | 862.5 | 0.617133 |
| 435 | 0.945725 | 877 | 0.602419 |
| 448.5 | 0.922838 | 890.5 | 0.604054 |
| 462.5 | 0.90976 | 904 | 0.602419 |
| 476.5 | 0.870525 | 917.5 | 0.600785 |
| 490.5 | 0.863986 | 931 | 0.602419 |
| 505.5 | 0.842733 | 943.5 | 0.597515 |
| 519.5 | 0.826385 | 953 | 0.59915 |

TABLE 6

DMSO CONCENTRATION IN TISSUE

| | PEAK AREA | % DMSO | DILUTION | FINAL (% DMSO) |
|---|---|---|---|---|
| VALVE A | 19711 | 0.205153894 | 11.04784689 | 2.266509 |
| VALVE B | 22669 | 0.235705433 | 8.128309572 | 1.915887 |
| VALVE C | 24930 | 0.259058046 | 10.96818664 | 2.841397 |
| | | | AVERAGE = | 2.341264 |

Figure 12:
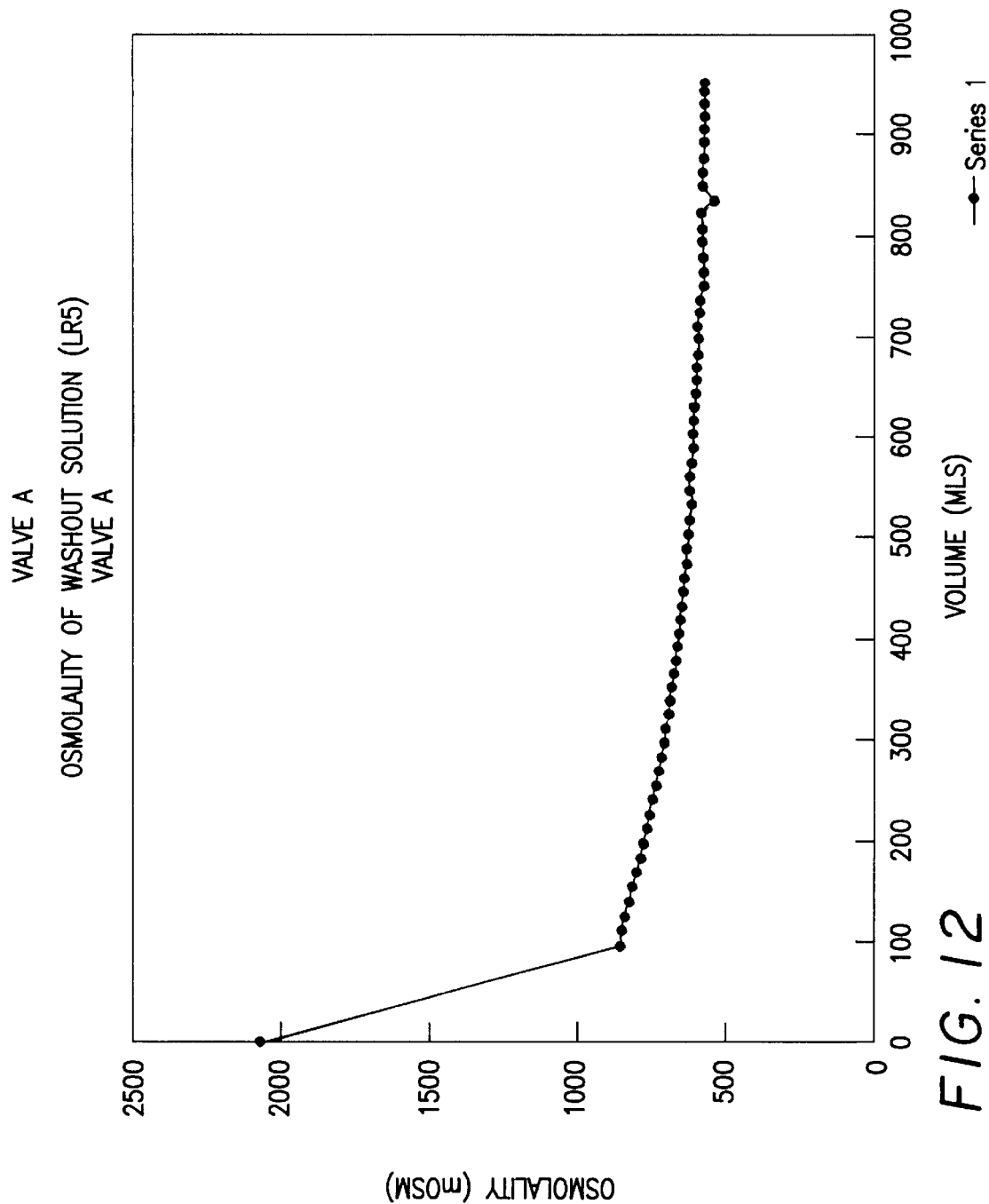
FIG. 12
Figure 13:
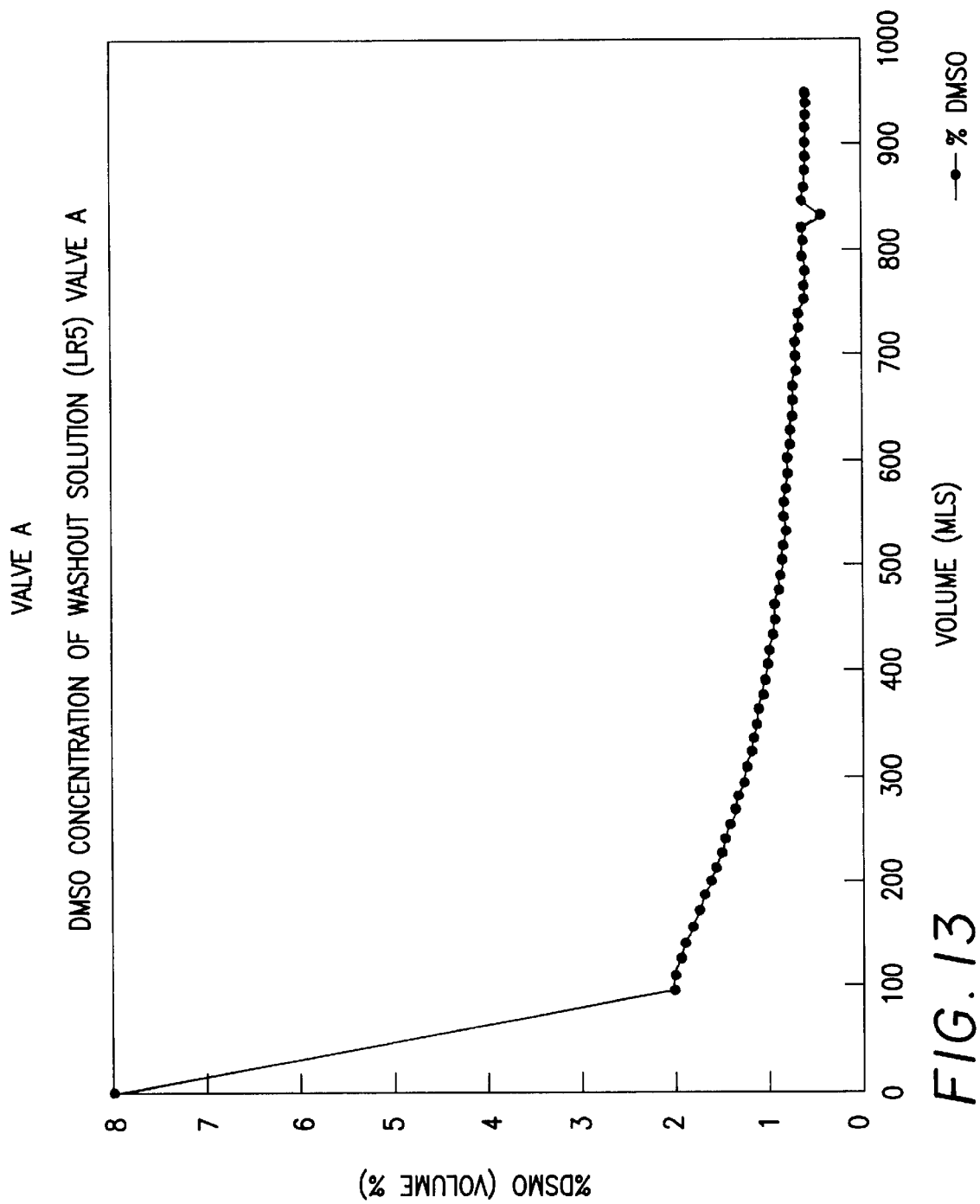
FIG. 13

The heart valves used in the wash-out procedures described in example 5 and FIGS. 12 and 13 (with tabular data shown in Table 4 and 5) were minced and extracted in 10% methanol in ultra pure water. The extract was then analyzed using reverse-phase high performance liquid chromatography and the tissue DMSO concentrations calculated as a volume percent. The results of three (3) separate wash-out procedures were used to calculate a mean and standard deviation for tissue concentrations of DMSO in heart valves processed using the continuous perfusion chamber with LR5 as the wash-out solution.

With the continuous perfusion chamber illustrated in FIG. 1, the wash-out solution was allowed to fill the continuous perfusion chamber. After the chamber filled and washout was completed, solution remained covering the tissue. At that point, greater than 95% of the original solution used in freezing the tissue had been removed from the continuous perfusion chamber and the osmolality of the remaining solution approximated that of the original wash-out solution, i.e. approximately 550 mOsm/KgH$_2$O. In addition, following completion of the method, the tissue concentration of cryoprotectant (for example dimethylsulfoxide) was less than 3.0% (average DMSO concentration of valve A, B and C was 2.341264%.

Example 6

Figure 4:
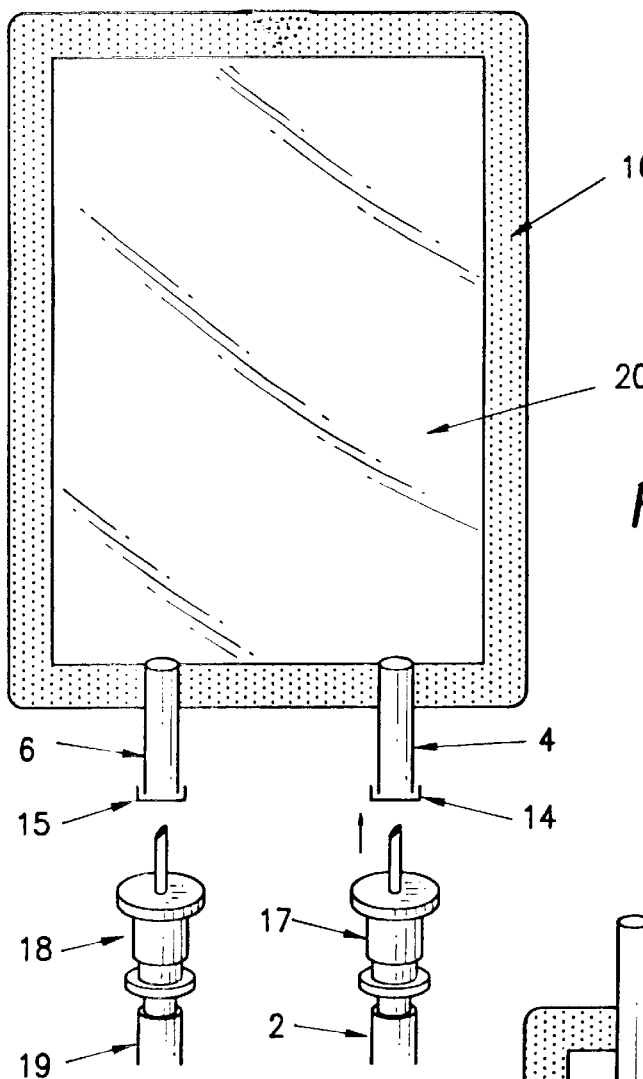
FIG. 4
Figure 5:
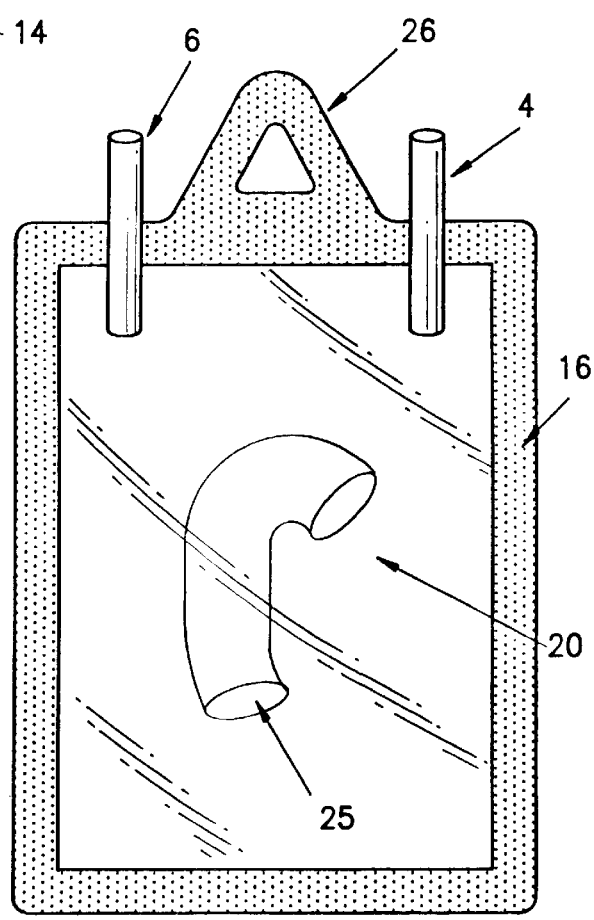
FIG. 5
Figure 6:
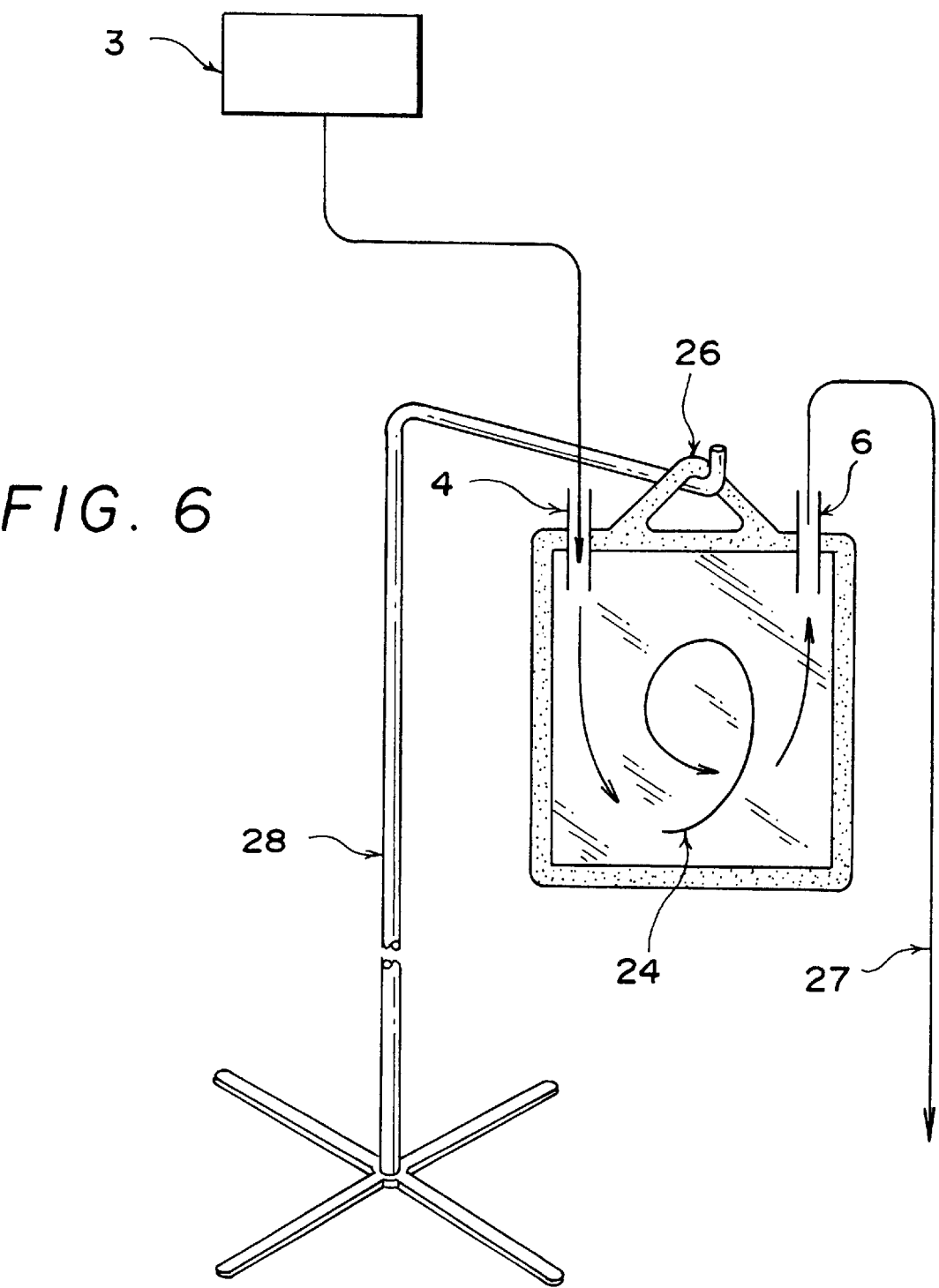
FIG. 6

As illustrated in FIGS. 4, 5, and 6, a cryopreserved human heart valve is removed from storage in an ultra low temperature storage container and subjected to transition. A one (1) liter bag of LR5 was hung from a standard "IV pole" (21 such as is normally available in a hospital) and positioned next to a counter/table top. The continuous perfusion chamber 1, which had been removed from its' sterile packaging and placed onto a sterile field on the counter/table top, was used to simultaneously effect tissue thawing and removal of cryoprotectant when the inlet line 2 (the line attached to the inlet port positioned along the seal of the deformable chamber) was inserted into the access port on the bag of LR5 such that saline solution began to flow into, through, and out of the deformable continuous perfusion chamber 1. While the chamber began to fill, the outlet port line 19 on the chamber was opened and placed such that it drained into the waste basin 23 located beneath the counter/table. At that time, the approximate operating pressure of the system was regulated by a wash-out solution height of 22 5 to 6 feet. The wash-out/thaw procedure required approximately 9 to 10 minuted and at the completion of the method, the thawed tissue was present in approximately 100 mls of hyperosmolar solution at approximately room, or ambient temperature. The osmolality of the solution exiting the continuous perfusion chamber versus time/volume changed from approximately 3000 mOsm/KgH$_2$O to approximately 550–600 KgH$_2$O and the final tissue concentration of dimethyl sulfoxide approximated less than 3.0%. The valve was then removed from the deformable continuous perfusion chamber and was ready for transplantation.

While the invention has been described in connection with specific embodiments thereof, it will be understood that it is capable of further modifications and this application is intended to cover any variations, uses, or adaptions of the invention following, in the principle of the invention and including such departures from the present disclosure as came within known or customary practice within the art to which the invention pertains and as may be applied to the essential features hereinbefore set forth as follows in the scope of the appended claims. All references including patents and co-pending patent applications cited herein are hereby incorporated herein by reference in their entirety.

What is claimed:

1. A continuous perfusion chamber assembly, comprising:
   a generally cylindrical body portion having an open top end and a closed bottom end, comprising:
   an inlet port located at a sidewall of said body portion disposed towards said bottom end;
   an outlet port located between said inlet port and said open top end of said body portion at a sidewall of said body portion, said inlet port is configured so that when solution is introduced into said body portion through said inlet port a circular flow of solution is effected, and
   a major basin, where said body portion is disposed in said major basin during use.

2. A continuous perfusion chamber, comprising:
   a generally cylindrical body portion having an open top end and a closed bottom end;
   an inlet port located at a sidewall of said body portion disposed towards said bottom end;
   an outlet port located between said inlet port and said open top end of said body portion at a sidewall of said body portion; and inflow tubing having a first end connected to a solution reservoir, and having a second end connected to said inlet port, where said inlet port is configured so that when solution is introduced into said body portion through said inlet port a circular flow of solution is effected.

3. A continuous perfusion chamber, comprising:

a generally cylindrical body portion having an open top end and a closed bottom end;

an inlet port located at a sidewall of said body portion disposed towards said bottom end;

an outlet port located between said inlet port and said open top end of said body portion at a sidewall of said body portion; and outflow tubing having a first end connected to said outlet port, and said outflow tubing having a second end directed to a waste container, where said inlet port is configured so that when solution is introduced into said body portion through said inlet port a circular flow of solution is effected.

4. The continuous perfusion chamber of claim 2, further comprising:

outflow tubing having a first end connected to said outlet port, and said outflow tubing having a second end directed to a waste container.

5. A continuous perfusion chamber assembly, comprising:

a deformable pouch comprising:

an inlet port located through a sidewall of said deformable pouch;

an outlet port located through a sidewall of said deformable pouch;

an inlet septum provided on said inlet port; and and out-flow septum provided on said outlet port, where said inlet port and said outlet port are configured such that when solution is introduced into said deformable pouch through said inlet port, a circular flow of solution is effected;

suspension means to suspend said continuous perfusion chamber; and a major basin where said continuous perfusion chamber is suspended in said major basin by said suspension means.

* * * * *